(12) United States Patent
Jacobson

(10) Patent No.: US 9,072,913 B2
(45) Date of Patent: Jul. 7, 2015

(54) RATE RESPONSIVE LEADLESS CARDIAC PACEMAKER

(75) Inventor: Peter M. Jacobson, Livermore, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 13/098,266

(22) Filed: Apr. 29, 2011

(65) Prior Publication Data

US 2011/0208260 A1  Aug. 25, 2011

Related U.S. Application Data

(63) Continuation of application No. 11/549,603, filed on Oct. 13, 2006, now Pat. No. 7,937,148.

(60) Provisional application No. 60/726,706, filed on Oct. 14, 2005, provisional application No. 60/761,531, (Continued)

(51) Int. Cl.
*A61N 1/00* (2006.01)
*A61N 1/39* (2006.01)
(Continued)

(52) U.S. Cl.
CPC .......... *A61N 1/3962* (2013.01); *A61M 25/0662* (2013.01); *A61N 1/056* (2013.01);
(Continued)

(58) Field of Classification Search
CPC ..... A61N 1/37; A61N 1/3702; A61N 1/3756; A61N 1/37288; A61N 1/3706; A61N 1/368; A61N 1/372; A61N 1/3727; A61N 1/3956
USPC ........... 607/9, 27, 32, 119, 122; 600/373, 374
See application file for complete search history.

(56) References Cited

U.S. PATENT DOCUMENTS 3,199,508 A  8/1965  Roth
3,212,496 A  10/1965  Preston
(Continued)

FOREIGN PATENT DOCUMENTS

EP  0362611 A1  4/1990
EP  1741465 A1  1/2007
(Continued)

OTHER PUBLICATIONS

U.S. Appl. No. 10/891,747 entitled "System and method for synchronizing supplemental pacing pulses generated by a satellite pacing device with primary pulses delivered by a separate pacing device," filed Jul. 14, 2004 (abandoned prior to pub.: CIP of this app. is U.S. Pat. 7,630,767).

(Continued)

*Primary Examiner* — Niketa Patel
*Assistant Examiner* — William Levicky
(74) *Attorney, Agent, or Firm* — Theresa A. Raymer

(57) ABSTRACT

A leadless cardiac pacemaker comprises a housing, a plurality of electrodes coupled to an outer surface of the housing, and a pulse delivery system hermetically contained within the housing and electrically coupled to the electrode plurality, the pulse delivery system configured for sourcing energy internal to the housing, generating and delivering electrical pulses to the electrode plurality. The pacemaker further comprises an activity sensor hermetically contained within the housing and adapted to sense activity and a processor hermetically contained within the housing and communicatively coupled to the pulse delivery system, the activity sensor, and the electrode plurality, the processor configured to control electrical pulse delivery at least partly based on the sensed activity.

9 Claims, 7 Drawing Sheets

Related U.S. Application Data filed on Jan. 24, 2006, provisional application No. 60/729,671, filed on Oct. 24, 2005, provisional application No. 60/737,296, filed on Nov. 16, 2005, provisional application No. 60/739,901, filed on Nov. 26, 2005, provisional application No. 60/749,017, filed on Dec. 10, 2005, provisional application No. 60/761,740, filed on Jan. 24, 2006.

(51) Int. Cl.
| | |
|---|---|
| *A61N 1/05* | (2006.01) |
| *A61N 1/362* | (2006.01) |
| *A61N 1/365* | (2006.01) |
| *A61N 1/368* | (2006.01) |
| *A61N 1/372* | (2006.01) |
| *A61N 1/375* | (2006.01) |
| *H04B 13/00* | (2006.01) |
| *A61N 1/37* | (2006.01) |
| *A61M 25/06* | (2006.01) |

(52) U.S. Cl.
CPC ......... *A61N 1/3627* (2013.01); *A61N 1/36514* (2013.01); *A61N 1/36542* (2013.01); *A61N 1/368* (2013.01); *A61N 1/3684* (2013.01); *A61N 1/372* (2013.01); *A61N 1/37205* (2013.01); *A61N 1/37217* (2013.01); *A61N 1/37252* (2013.01); *A61N 1/3727* (2013.01); *A61N 1/37288* (2013.01); *A61N 1/375* (2013.01); *A61N 1/3756* (2013.01); *A61N 1/3956* (2013.01); *A61N 2001/058* (2013.01); *H04B 13/005* (2013.01); *A61N 1/0587* (2013.01); *A61N 1/3706* (2013.01); *A61N 1/3704* (2013.01)

(56) References Cited

U.S. PATENT DOCUMENTS

| | | | |
|---|---|---|---|
| 3,218,638 A | 11/1965 | Honig | |
| 3,241,556 A | 3/1966 | Zacouto | |
| 3,478,746 A | 11/1969 | Greatbatch | |
| 3,603,881 A | 9/1971 | Thornton | |
| 3,727,616 A | 4/1973 | Lenzkes | |
| 3,757,778 A | 9/1973 | Graham | |
| 3,823,708 A | 7/1974 | Lawhorn | |
| 3,830,228 A | 8/1974 | Foner | |
| 3,835,864 A | 9/1974 | Rasor et al. | |
| 3,836,798 A | 9/1974 | Greatbatch | |
| 3,870,051 A | 3/1975 | Brindley | |
| 3,872,251 A | 3/1975 | Auerbach et al. | |
| 3,905,364 A | 9/1975 | Cudahy et al. | |
| 3,940,692 A | 2/1976 | Neilson et al. | |
| 3,943,926 A | 3/1976 | Barragan | |
| 3,943,936 A * | 3/1976 | Rasor et al. | 607/35 |
| 3,946,744 A | 3/1976 | Auerbach | |
| 3,952,750 A | 4/1976 | Mirowski et al. | |
| 4,027,663 A | 6/1977 | Fischler et al. | |
| 4,072,154 A | 2/1978 | Anderson et al. | |
| 4,083,366 A | 4/1978 | Gombrich et al. | |
| 4,087,389 A | 5/1978 | Coppola | |
| 4,102,344 A | 7/1978 | Conway et al. | |
| 4,146,029 A | 3/1979 | Ellinwood, Jr. | |
| 4,151,513 A | 4/1979 | Menken et al. | |
| 4,151,540 A | 4/1979 | Sander et al. | |
| 4,152,540 A | 5/1979 | Duncan et al. | |
| 4,173,221 A | 11/1979 | McLaughlin et al. | |
| 4,187,854 A | 2/1980 | Hepp et al. | |
| 4,210,149 A | 7/1980 | Heilman et al. | |
| RE30,366 E | 8/1980 | Rasor et al. | |
| 4,223,678 A | 9/1980 | Langer et al. | |
| 4,250,888 A | 2/1981 | Grosskopf | |
| 4,256,115 A | 3/1981 | Bilitch | |
| 4,296,756 A | 10/1981 | Dunning et al. | |
| 4,310,000 A | 1/1982 | Lindemans | |
| 4,312,354 A | 1/1982 | Walters | |
| 4,318,412 A | 3/1982 | Stanly et al. | |
| 4,336,810 A | 6/1982 | Anderson et al. | |
| 4,350,169 A | 9/1982 | Dutcher et al. | |
| 4,374,382 A | 2/1983 | Markowitz | |
| 4,406,288 A | 9/1983 | Horwinski et al. | |
| 4,411,271 A | 10/1983 | Markowitz | |
| 4,418,695 A | 12/1983 | Buffet | |
| 4,424,551 A | 1/1984 | Stevenson et al. | |
| 4,428,378 A | 1/1984 | Anderson et al. | |
| 4,440,173 A | 4/1984 | Hudziak et al. | |
| 4,442,840 A | 4/1984 | Wojciechowicz, Jr. | |
| 4,453,162 A | 6/1984 | Money et al. | |
| 4,458,692 A | 7/1984 | Simson | |
| 4,481,950 A | 11/1984 | Duggan | |
| 4,513,743 A | 4/1985 | van Arragon et al. | |
| 4,516,579 A | 5/1985 | Irnich | |
| 4,522,208 A | 6/1985 | Buffet | |
| 4,524,774 A | 6/1985 | Hildebrandt | |
| 4,531,527 A | 7/1985 | Reinhold, Jr. et al. | |
| 4,543,955 A * | 10/1985 | Schroeppel | 600/348 |
| 4,550,370 A | 10/1985 | Baker | |
| 4,552,127 A | 11/1985 | Schiff | |
| 4,552,154 A | 11/1985 | Hartlaub | |
| 4,562,846 A | 1/1986 | Cox et al. | |
| 4,586,508 A | 5/1986 | Batina et al. | |
| 4,606,352 A | 8/1986 | Geddes et al. | |
| 4,607,639 A | 8/1986 | Tanagho et al. | |
| 4,612,934 A | 9/1986 | Borkan | |
| 4,625,730 A | 12/1986 | Fountain et al. | |
| 4,679,144 A | 7/1987 | Cox et al. | |
| 4,681,111 A | 7/1987 | Silvian | |
| 4,681,117 A | 7/1987 | Brodman et al. | |
| 4,702,253 A | 10/1987 | Nappholz et al. | |
| 4,719,920 A | 1/1988 | Alt et al. | |
| 4,722,342 A | 2/1988 | Amundson | |
| 4,750,495 A | 6/1988 | Moore et al. | |
| 4,763,340 A | 8/1988 | Yoneda et al. | |
| 4,763,655 A | 8/1988 | Wirtzfeld et al. | |
| 4,787,389 A | 11/1988 | Tarjan | |
| 4,791,931 A | 12/1988 | Slate | |
| 4,793,353 A | 12/1988 | Borkan | |
| 4,794,532 A | 12/1988 | Leckband et al. | |
| 4,802,481 A | 2/1989 | Schroeppel | |
| 4,809,697 A | 3/1989 | Causey, III et al. | |
| 4,827,940 A | 5/1989 | Mayer et al. | |
| 4,830,006 A | 5/1989 | Haluska et al. | |
| 4,844,076 A | 7/1989 | Lesho et al. | |
| 4,846,195 A | 7/1989 | Alt | |
| 4,858,610 A | 8/1989 | Callaghan et al. | |
| 4,860,750 A | 8/1989 | Frey et al. | |
| 4,875,483 A | 10/1989 | Vollmann et al. | |
| 4,880,004 A | 11/1989 | Baker, Jr. et al. | |
| 4,883,064 A | 11/1989 | Olson et al. | |
| 4,886,064 A | 12/1989 | Strandberg | |
| 4,896,068 A | 1/1990 | Nilsson | |
| 4,903,701 A | 2/1990 | Moore et al. | |
| 4,905,708 A | 3/1990 | Davies | |
| 4,926,863 A | 5/1990 | Alt | |
| 4,974,589 A | 12/1990 | Sholder | |
| 4,987,897 A * | 1/1991 | Funke | 607/32 |
| 4,995,390 A | 2/1991 | Cook et al. | |
| 5,010,887 A | 4/1991 | Thornander | |
| 5,012,806 A | 5/1991 | De Bellis | |
| 5,014,701 A | 5/1991 | Pless et al. | |
| 5,040,533 A | 8/1991 | Fearnot | |
| 5,040,534 A | 8/1991 | Mann et al. | |
| 5,040,536 A | 8/1991 | Riff | |
| 5,042,497 A | 8/1991 | Shapland | |
| 5,052,399 A | 10/1991 | Olive et al. | |
| 5,058,581 A | 10/1991 | Silvian | |
| 5,065,759 A | 11/1991 | Begemann et al. | |
| 5,076,270 A | 12/1991 | Stutz, Jr. | |
| 5,076,272 A | 12/1991 | Ferek-Petric | |
| 5,085,224 A | 2/1992 | Galen et al. | |
| 5,086,772 A | 2/1992 | Larnard et al. | |
| 5,088,488 A | 2/1992 | Markowitz et al. | |

(56) References Cited

U.S. PATENT DOCUMENTS

| | | | |
|---|---|---|---|
| 5,095,903 A | 3/1992 | DeBellis | |
| 5,109,845 A | 5/1992 | Yuuchi et al. | |
| 5,111,816 A | 5/1992 | Pless et al. | |
| 5,113,859 A | 5/1992 | Funke | |
| 5,113,869 A | 5/1992 | Nappholz et al. | |
| 5,133,350 A | 7/1992 | Duffin | |
| 5,135,004 A | 8/1992 | Adams et al. | |
| 5,170,784 A | 12/1992 | Ramon et al. | |
| 5,170,802 A | 12/1992 | Mehra | |
| 5,179,947 A | 1/1993 | Meyerson et al. | |
| 5,184,616 A | 2/1993 | Weiss | |
| 5,193,539 A | 3/1993 | Schulman et al. | |
| 5,193,540 A | 3/1993 | Schulman et al. | |
| 5,193,550 A | 3/1993 | Duffin | |
| 5,217,010 A | 6/1993 | Tsitlik et al. | |
| 5,247,945 A | 9/1993 | Heinze et al. | |
| 5,259,394 A | 11/1993 | Bens | |
| 5,260,621 A | 11/1993 | Little et al. | |
| 5,267,150 A | 11/1993 | Wilkinson | |
| 5,282,841 A | 2/1994 | Szyszkowski | |
| 5,284,136 A | 2/1994 | Hauck et al. | |
| 5,291,902 A | 3/1994 | Carman | |
| 5,300,093 A | 4/1994 | Koestner et al. | |
| 5,304,206 A | 4/1994 | Baker, Jr. et al. | |
| 5,304,209 A | 4/1994 | Adams et al. | |
| 5,313,953 A | 5/1994 | Yomtov et al. | |
| 5,318,596 A | 6/1994 | Barreras et al. | |
| 5,331,966 A * | 7/1994 | Bennett et al. | 600/508 |
| 5,333,095 A | 7/1994 | Stevenson et al. | |
| 5,336,244 A | 8/1994 | Weijand | |
| 5,342,401 A | 8/1994 | Spano et al. | |
| 5,354,317 A | 10/1994 | Alt | |
| 5,358,514 A | 10/1994 | Schulman et al. | |
| 5,373,852 A | 12/1994 | Harrison et al. | |
| 5,383,912 A | 1/1995 | Cox et al. | |
| 5,383,915 A | 1/1995 | Adams | |
| 5,404,877 A | 4/1995 | Nolan et al. | |
| 5,405,367 A | 4/1995 | Schulman et al. | |
| 5,406,444 A | 4/1995 | Selfried et al. | |
| 5,411,532 A | 5/1995 | Mortazavi | |
| 5,411,535 A * | 5/1995 | Fujii et al. | 607/32 |
| 5,411,537 A | 5/1995 | Munshi et al. | |
| 5,417,222 A | 5/1995 | Dempsey et al. | |
| 5,419,337 A | 5/1995 | Dempsey et al. | |
| 5,431,171 A | 7/1995 | Harrison et al. | |
| 5,446,447 A | 8/1995 | Carney et al. | |
| 5,456,261 A | 10/1995 | Luczyk | |
| 5,466,246 A | 11/1995 | Silvian | |
| 5,469,857 A | 11/1995 | Laurent et al. | |
| 5,480,415 A | 1/1996 | Cox et al. | |
| 5,481,262 A | 1/1996 | Urbas et al. | |
| 5,522,876 A | 6/1996 | Rusink | |
| 5,531,779 A | 7/1996 | Dahl et al. | |
| 5,531,781 A | 7/1996 | Alferness et al. | |
| 5,531,783 A | 7/1996 | Giele et al. | |
| 5,539,775 A | 7/1996 | Tuttle et al. | |
| 5,549,654 A | 8/1996 | Powell | |
| 5,549,659 A | 8/1996 | Johansen et al. | |
| 5,551,427 A | 9/1996 | Altman | |
| 5,556,421 A | 9/1996 | Prutchi et al. | |
| 5,562,717 A | 10/1996 | Tippey et al. | |
| 5,571,143 A | 11/1996 | Hoegnelid et al. | |
| 5,571,148 A | 11/1996 | Loeb et al. | |
| 5,579,775 A | 12/1996 | Dempsey et al. | |
| 5,586,556 A | 12/1996 | Spivey et al. | |
| 5,591,217 A | 1/1997 | Barreras | |
| 5,598,848 A | 2/1997 | Swanson et al. | |
| 5,649,952 A | 7/1997 | Lam | |
| 5,650,759 A | 7/1997 | Hittman et al. | |
| 5,654,984 A | 8/1997 | Hershbarger et al. | |
| 5,662,689 A | 9/1997 | Elsberry et al. | |
| 5,669,391 A * | 9/1997 | Williams | 600/510 |
| 5,674,259 A | 10/1997 | Gray | |
| 5,676,153 A | 10/1997 | Smith et al. | |
| 5,693,076 A | 12/1997 | Kaemmerer | |
| 5,694,940 A | 12/1997 | Unger et al. | |
| 5,694,952 A | 12/1997 | Lidman et al. | |
| 5,697,958 A | 12/1997 | Paul et al. | |
| 5,702,427 A | 12/1997 | Ecker et al. | |
| 5,725,559 A | 3/1998 | Alt et al. | |
| 5,728,154 A | 3/1998 | Crossett et al. | |
| 5,730,143 A | 3/1998 | Schwarzberg | |
| 5,735,880 A * | 4/1998 | Prutchi et al. | 607/9 |
| 5,738,102 A | 4/1998 | Lemelson | |
| 5,740,811 A | 4/1998 | Hedberg et al. | |
| 5,741,314 A | 4/1998 | Daly et al. | |
| 5,766,231 A | 6/1998 | Erickson et al. | |
| 5,792,202 A | 8/1998 | Rueter | |
| 5,792,205 A | 8/1998 | Alt et al. | |
| 5,810,735 A | 9/1998 | Halperin et al. | |
| 5,814,076 A | 9/1998 | Brownlee | |
| 5,814,087 A | 9/1998 | Renirie | |
| 5,814,089 A * | 9/1998 | Stokes et al. | 607/32 |
| 5,824,016 A | 10/1998 | Ekwall | |
| 5,871,451 A | 2/1999 | Unger et al. | |
| 5,876,353 A | 3/1999 | Riff | |
| 5,876,425 A | 3/1999 | Gord et al. | |
| 5,891,178 A | 4/1999 | Mann et al. | |
| 5,899,928 A * | 5/1999 | Sholder et al. | 607/27 |
| 5,935,079 A | 8/1999 | Swanson et al. | |
| 5,954,761 A | 9/1999 | Machek et al. | |
| 5,957,861 A | 9/1999 | Combs et al. | |
| 5,984,861 A | 11/1999 | Crowley | |
| 5,987,352 A | 11/1999 | Klein et al. | |
| 5,995,876 A | 11/1999 | Kruse et al. | |
| 5,999,857 A | 12/1999 | Weijand et al. | |
| 6,002,969 A | 12/1999 | Machek et al. | |
| 6,004,269 A | 12/1999 | Crowley et al. | |
| 6,061,596 A | 5/2000 | Richmond et al. | |
| 6,076,016 A | 6/2000 | Feierbach | |
| 6,080,187 A | 6/2000 | Alt et al. | |
| 6,093,146 A | 7/2000 | Filangeri | |
| 6,096,065 A | 8/2000 | Crowley | |
| 6,102,874 A | 8/2000 | Stone et al. | |
| 6,112,116 A | 8/2000 | Fischell et al. | |
| 6,115,628 A | 9/2000 | Stadler et al. | |
| 6,115,630 A | 9/2000 | Stadler et al. | |
| 6,115,636 A | 9/2000 | Ryan | |
| 6,119,031 A | 9/2000 | Crowley | |
| 6,125,290 A | 9/2000 | Miesel | |
| 6,125,291 A | 9/2000 | Miesel et al. | |
| 6,128,526 A | 10/2000 | Stadler et al. | |
| 6,129,751 A | 10/2000 | Lucchesi et al. | |
| 6,132,390 A | 10/2000 | Cookston et al. | |
| 6,132,456 A | 10/2000 | Sommer et al. | |
| 6,134,459 A | 10/2000 | Roberts et al. | |
| 6,134,470 A | 10/2000 | Hartlaub | |
| 6,139,510 A | 10/2000 | Palermo | |
| 6,141,584 A | 10/2000 | Rockwell et al. | |
| 6,141,588 A | 10/2000 | Cox et al. | |
| 6,141,592 A | 10/2000 | Pauly | |
| 6,144,866 A | 11/2000 | Miesel et al. | |
| 6,148,230 A | 11/2000 | KenKnight | |
| 6,152,882 A | 11/2000 | Prutchi | |
| 6,163,723 A | 12/2000 | Roberts et al. | |
| 6,164,284 A | 12/2000 | Schulman et al. | |
| 6,167,310 A | 12/2000 | Grevious | |
| 6,178,349 B1 | 1/2001 | Kieval | |
| 6,178,356 B1 | 1/2001 | Chastain et al. | |
| 6,185,443 B1 | 2/2001 | Crowley | |
| 6,185,452 B1 | 2/2001 | Schulman et al. | |
| 6,185,464 B1 | 2/2001 | Bonner et al. | |
| 6,188,932 B1 | 2/2001 | Lindegren | |
| 6,190,324 B1 | 2/2001 | Kieval et al. | |
| 6,198,952 B1 | 3/2001 | Miesel | |
| 6,201,993 B1 | 3/2001 | Kruse et al. | |
| 6,208,894 B1 | 3/2001 | Schulman et al. | |
| 6,208,900 B1 | 3/2001 | Ecker et al. | |
| 6,223,081 B1 | 4/2001 | Kerver | |
| 6,230,059 B1 | 5/2001 | Duffin | |
| 6,236,882 B1 | 5/2001 | Lee et al. | |
| 6,240,321 B1 | 5/2001 | Janke et al. | |
| 6,243,608 B1 | 6/2001 | Pauly et al. | |
| 6,248,080 B1 | 6/2001 | Miesel et al. | |

(56) References Cited

U.S. PATENT DOCUMENTS

| | | |
|---|---|---|
| 6,263,245 B1 | 7/2001 | Snell |
| 6,265,100 B1 | 7/2001 | Saaski et al. |
| 6,266,554 B1 | 7/2001 | Hsu et al. |
| 6,266,564 B1 | 7/2001 | Hill et al. |
| 6,272,379 B1 | 8/2001 | Fischell et al. |
| 6,280,409 B1 | 8/2001 | Stone et al. |
| 6,289,229 B1 | 9/2001 | Crowley |
| 6,306,088 B1 | 10/2001 | Krausman et al. |
| 6,310,960 B1 | 10/2001 | Saaski et al. |
| 6,315,721 B2 | 11/2001 | Schulman et al. |
| 6,324,418 B1 | 11/2001 | Crowley et al. |
| 6,324,421 B1 | 11/2001 | Stadler et al. |
| RE37,463 E | 12/2001 | Altman |
| 6,343,227 B1 | 1/2002 | Crowley |
| 6,343,233 B1 | 1/2002 | Werner et al. |
| 6,347,245 B1 | 2/2002 | Lee et al. |
| 6,358,202 B1 | 3/2002 | Arent |
| 6,361,522 B1 | 3/2002 | Scheiner et al. |
| 6,363,282 B1 | 3/2002 | Nichols et al. |
| 6,364,831 B1 | 4/2002 | Crowley |
| 6,370,434 B1 | 4/2002 | Zhang et al. |
| 6,381,492 B1 | 4/2002 | Rockwell et al. |
| 6,381,493 B1 | 4/2002 | Stadler et al. |
| 6,381,494 B1 | 4/2002 | Gilkerson et al. |
| 6,383,209 B1 | 5/2002 | Crowley |
| 6,385,593 B2 | 5/2002 | Linberg |
| 6,386,882 B1 | 5/2002 | Linberg |
| 6,397,100 B2 | 5/2002 | Stadler et al. |
| 6,402,689 B1 | 6/2002 | Scarantino et al. |
| 6,405,073 B1 | 6/2002 | Crowley et al. |
| 6,405,083 B1 | 6/2002 | Rockwell et al. |
| 6,409,674 B1 | 6/2002 | Brockway et al. |
| 6,409,675 B1 | 6/2002 | Turcott |
| 6,412,490 B1 | 7/2002 | Lee |
| 6,418,346 B1 | 7/2002 | Nelson et al. |
| 6,423,056 B1 | 7/2002 | Ishikawa et al. |
| 6,424,866 B2 | 7/2002 | Mika et al. |
| 6,428,484 B1 | 8/2002 | Battmer et al. |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,442,433 B1 | 8/2002 | Linberg |
| 6,444,970 B1 | 9/2002 | Barbato |
| 6,445,953 B1 | 9/2002 | Bulkes et al. |
| 6,458,145 B1 | 10/2002 | Ravenscroft et al. |
| 6,459,928 B2 | 10/2002 | Mika et al. |
| 6,459,937 B1 | 10/2002 | Morgan et al. |
| 6,466,820 B1 | 10/2002 | Juran et al. |
| 6,468,263 B1 | 10/2002 | Fischell et al. |
| 6,470,215 B1 | 10/2002 | Kraus et al. |
| 6,471,645 B1 | 10/2002 | Warkentin et al. |
| 6,472,991 B1 | 10/2002 | Schulman et al. |
| 6,477,424 B1 | 11/2002 | Thompson et al. |
| 6,480,733 B1 | 11/2002 | Turcott |
| 6,482,154 B1 | 11/2002 | Haubrich et al. |
| 6,484,055 B1 | 11/2002 | Marcovecchio |
| 6,484,057 B2 | 11/2002 | Ideker et al. |
| 6,490,487 B1 | 12/2002 | Kraus et al. |
| 6,496,715 B1 | 12/2002 | Lee et al. |
| 6,498,951 B1 | 12/2002 | Larson et al. |
| 6,500,168 B1 | 12/2002 | Jellie |
| 6,501,983 B1 | 12/2002 | Natarajan et al. |
| 6,512,949 B1 | 1/2003 | Combs et al. |
| 6,512,959 B1 | 1/2003 | Gomperz et al. |
| 6,522,926 B1 | 2/2003 | Kieval et al. |
| 6,522,928 B2 | 2/2003 | Whitehurst et al. |
| 6,539,257 B1 | 3/2003 | KenKnight |
| 6,542,781 B1 | 4/2003 | Koblish et al. |
| 6,556,860 B1 | 4/2003 | Groenewegen |
| 6,558,321 B1 | 5/2003 | Burd et al. |
| 6,564,807 B1 | 5/2003 | Schulman et al. |
| 6,567,680 B2 | 5/2003 | Swetlik et al. |
| 6,571,120 B2 | 5/2003 | Hutten |
| 6,574,509 B1 | 6/2003 | Kraus et al. |
| 6,574,511 B2 | 6/2003 | Lee |
| 6,580,946 B2 | 6/2003 | Struble |
| 6,580,948 B2 | 6/2003 | Haupert et al. |
| 6,584,351 B1 | 6/2003 | Ekwall |
| 6,584,352 B2 | 6/2003 | Combs et al. |
| 6,589,187 B1 | 7/2003 | Dirnberger et al. |
| 6,592,518 B2 | 7/2003 | Denker et al. |
| 6,594,523 B1 | 7/2003 | Levine |
| 6,597,948 B1 | 7/2003 | Rockwell et al. |
| 6,597,952 B1 | 7/2003 | Mika et al. |
| 6,609,023 B1 | 8/2003 | Fischell et al. |
| 6,611,710 B2 | 8/2003 | Gomperz et al. |
| 6,615,075 B2 | 9/2003 | Mlynash et al. |
| 6,622,043 B1 | 9/2003 | Kraus et al. |
| 6,647,292 B1 | 11/2003 | Bardy et al. |
| 6,648,823 B2 | 11/2003 | Thompson |
| 6,649,078 B2 | 11/2003 | Yu |
| 6,654,638 B1 | 11/2003 | Sweeney |
| 6,658,285 B2 | 12/2003 | Potse et al. |
| 6,658,297 B2 | 12/2003 | Loeb |
| 6,658,301 B2 | 12/2003 | Loeb et al. |
| 6,659,959 B2 | 12/2003 | Brockway et al. |
| 6,669,631 B2 | 12/2003 | Norris et al. |
| 6,681,135 B1 | 1/2004 | Davis et al. |
| 6,684,100 B1 | 1/2004 | Sweeney et al. |
| 6,687,540 B2 | 2/2004 | Marcovecchio |
| 6,687,546 B2 | 2/2004 | Lebel et al. |
| 6,689,117 B2 | 2/2004 | Sweeney et al. |
| 6,690,959 B2 | 2/2004 | Thompson |
| 6,694,191 B2 | 2/2004 | Starkweather et al. |
| 6,695,885 B2 | 2/2004 | Schulman et al. |
| 6,697,672 B2 | 2/2004 | Andersson |
| 6,697,677 B2 | 2/2004 | Dahl et al. |
| 6,699,200 B2 | 3/2004 | Cao et al. |
| 6,702,857 B2 | 3/2004 | Brauker et al. |
| 6,704,602 B2 * | 3/2004 | Berg et al. .................. 607/60 |
| 6,711,440 B2 | 3/2004 | Deal et al. |
| 6,716,238 B2 | 4/2004 | Elliott |
| 6,721,597 B1 | 4/2004 | Bardy et al. |
| 6,728,572 B2 | 4/2004 | Hsu et al. |
| 6,728,574 B2 | 4/2004 | Ujhelyi et al. |
| 6,728,576 B2 | 4/2004 | Thompson et al. |
| 6,731,976 B2 | 5/2004 | Penn et al. |
| 6,731,979 B2 | 5/2004 | MacDonald |
| 6,733,485 B1 | 5/2004 | Whitehurst et al. |
| 6,735,474 B1 | 5/2004 | Loeb et al. |
| 6,735,475 B1 | 5/2004 | Whitehurst et al. |
| 6,738,670 B1 | 5/2004 | Almendinger et al. |
| 6,741,877 B1 | 5/2004 | Shults et al. |
| 6,741,886 B2 | 5/2004 | Yonce |
| 6,746,404 B2 | 6/2004 | Schwartz |
| 6,754,538 B2 | 6/2004 | Linberg |
| 6,760,620 B2 | 7/2004 | Sippens Groenewegen |
| 6,764,446 B2 | 7/2004 | Wolinsky et al. |
| 6,768,923 B2 | 7/2004 | Ding et al. |
| 6,783,499 B2 | 8/2004 | Schwartz |
| 6,785,576 B2 | 8/2004 | Verness |
| 6,786,860 B2 | 9/2004 | Maltan et al. |
| 6,792,314 B2 | 9/2004 | Byers et al. |
| 6,799,069 B2 | 9/2004 | Weiner et al. |
| 6,804,559 B1 | 10/2004 | Kraus et al. |
| 6,804,561 B2 | 10/2004 | Stover |
| 6,809,507 B2 | 10/2004 | Morgan et al. |
| 6,811,533 B2 | 11/2004 | Lebel et al. |
| 6,813,519 B2 | 11/2004 | Lebel et al. |
| 6,821,154 B1 | 11/2004 | Canfield et al. |
| 6,823,217 B2 | 11/2004 | Rutten et al. |
| 6,824,512 B2 | 11/2004 | Warkentin et al. |
| 6,829,508 B2 | 12/2004 | Schulman et al. |
| 6,839,596 B2 | 1/2005 | Nelson et al. |
| 6,848,052 B2 | 1/2005 | Hamid et al. |
| 6,850,801 B2 | 2/2005 | Kieval et al. |
| 6,856,835 B2 | 2/2005 | Bardy et al. |
| 6,862,465 B2 | 3/2005 | Shults et al. |
| 6,862,480 B2 | 3/2005 | Cohen et al. |
| 6,865,420 B1 | 3/2005 | Kroll |
| 6,869,404 B2 | 3/2005 | Schulhauser et al. |
| 6,871,099 B1 | 3/2005 | Whitehurst et al. |
| 6,878,112 B2 | 4/2005 | Linberg et al. |
| 6,879,695 B2 | 4/2005 | Maltan et al. |

(56) References Cited

U.S. PATENT DOCUMENTS

| | | | |
|---|---|---|---|
| 6,879,855 B2 | 4/2005 | Schulman et al. |
| 6,882,875 B1 | 4/2005 | Crowley |
| 6,889,081 B2 | 5/2005 | Hsu |
| 6,893,395 B1 | 5/2005 | Kraus et al. |
| 6,895,279 B2 | 5/2005 | Loeb et al. |
| 6,895,281 B1 | 5/2005 | Amundson et al. |
| 6,896,651 B2 | 5/2005 | Gross et al. |
| 6,897,788 B2 | 5/2005 | Khair et al. |
| 6,901,294 B1 | 5/2005 | Whitehurst et al. |
| 6,901,296 B1 | 5/2005 | Whitehurst et al. |
| 6,907,285 B2 | 6/2005 | Denker et al. |
| 6,907,293 B2 | 6/2005 | Grill et al. |
| 6,912,420 B2 | 6/2005 | Scheiner et al. |
| 6,917,833 B2 | 7/2005 | Denker et al. |
| 6,925,328 B2 | 8/2005 | Foster et al. |
| 6,931,327 B2 | 8/2005 | Goode, Jr. et al. |
| 6,999,821 B2 | 2/2006 | Jenney et al. |
| 7,001,372 B2 | 2/2006 | Richter |
| 7,023,359 B2 | 4/2006 | Goetz et al. |
| 7,027,876 B2 | 4/2006 | Casavant et al. |
| 7,146,222 B2 | 12/2006 | Boling |
| 7,146,225 B2 | 12/2006 | Guenst et al. |
| 7,164,950 B2 | 1/2007 | Kroll et al. |
| 7,181,505 B2 | 2/2007 | Haller et al. |
| 7,187,971 B2 | 3/2007 | Sommer et al. |
| 7,200,437 B1 * | 4/2007 | Nabutovsky et al. ............ 607/9 |
| 7,212,870 B1 | 5/2007 | Helland |
| 7,277,754 B2 | 10/2007 | McCabe et al. |
| 7,289,853 B1 | 10/2007 | Campbell et al. |
| 7,307,544 B2 * | 12/2007 | Kim et al. ............... 340/870.07 |
| 7,363,090 B2 | 4/2008 | Halperin et al. |
| 7,558,631 B2 | 7/2009 | Cowan et al. |
| 7,565,195 B1 * | 7/2009 | Kroll et al. ......................... 607/2 |
| 7,616,991 B2 | 11/2009 | Mann et al. |
| 7,630,767 B1 * | 12/2009 | Poore et al. ...................... 607/32 |
| 7,634,313 B1 | 12/2009 | Kroll et al. |
| 7,650,186 B2 | 1/2010 | Hastings et al. |
| 7,848,823 B2 | 12/2010 | Drasler et al. |
| 7,937,148 B2 | 5/2011 | Jacobson |
| 7,945,333 B2 | 5/2011 | Jacobson |
| 8,010,209 B2 | 8/2011 | Jacobson |
| 8,295,939 B2 | 10/2012 | Jacobson |
| 8,788,053 B2 * | 7/2014 | Jacobson ......................... 607/60 |
| 2001/0031999 A1 | 10/2001 | Carter et al. |
| 2002/0032467 A1 | 3/2002 | Shemer et al. |
| 2002/0077686 A1 | 6/2002 | Westlund et al. |
| 2002/0116028 A1 | 8/2002 | Greatbatch et al. |
| 2002/0147488 A1 | 10/2002 | Doan et al. |
| 2003/0141995 A1 * | 7/2003 | Lin ................................. 341/52 |
| 2003/0158584 A1 | 8/2003 | Cates et al. |
| 2003/0163184 A1 | 8/2003 | Scheiner et al. |
| 2003/0199941 A1 | 10/2003 | Nielsen et al. |
| 2004/0011366 A1 | 1/2004 | Schulman et al. |
| 2004/0059392 A1 | 3/2004 | Parramon et al. |
| 2004/0116939 A1 | 6/2004 | Goode |
| 2004/0133242 A1 | 7/2004 | Chapman et al. |
| 2004/0143262 A1 | 7/2004 | Visram et al. |
| 2004/0147973 A1 | 7/2004 | Hauser |
| 2004/0167587 A1 | 8/2004 | Thompson |
| 2004/0172116 A1 | 9/2004 | Seifert et al. |
| 2004/0193223 A1 | 9/2004 | Kramer et al. |
| 2004/0249417 A1 | 12/2004 | Ransbury et al. |
| 2004/0260349 A1 | 12/2004 | Stroebel |
| 2005/0038474 A1 | 2/2005 | Wool |
| 2005/0038491 A1 | 2/2005 | Haack |
| 2005/0043765 A1 | 2/2005 | Williams et al. |
| 2005/0075682 A1 | 4/2005 | Schulman et al. |
| 2005/0096702 A1 | 5/2005 | Denker et al. |
| 2005/0131478 A1 | 6/2005 | Kim et al. |
| 2005/0149138 A1 | 7/2005 | Min et al. |
| 2005/0165465 A1 | 7/2005 | Pianca et al. |
| 2005/0267555 A1 | 12/2005 | Marnfeldt et al. |
| 2005/0288722 A1 | 12/2005 | Eigler et al. |
| 2006/0064149 A1 * | 3/2006 | Belacazar et al. ............ 607/122 |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0105613 A1 | 5/2006 | Carroll |
| 2006/0108335 A1 | 5/2006 | Zhao et al. |
| 2006/0121475 A1 | 6/2006 | Davids et al. |
| 2006/0135999 A1 | 6/2006 | Bodner et al. |
| 2006/0136004 A1 * | 6/2006 | Cowan et al. ................... 607/33 |
| 2006/0161222 A1 | 7/2006 | Haubrich et al. |
| 2006/0241705 A1 | 10/2006 | Neumann et al. |
| 2006/0247750 A1 | 11/2006 | Seifert et al. |
| 2006/0282150 A1 | 12/2006 | Olson et al. |
| 2007/0016263 A1 | 1/2007 | Armstrong et al. |
| 2007/0043414 A1 | 2/2007 | Fifer et al. |
| 2007/0055184 A1 | 3/2007 | Echt et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088418 A1 | 4/2007 | Jacobson |
| 2007/0123923 A1 | 5/2007 | Lindstrom et al. |
| 2007/0142709 A1 | 6/2007 | Martone et al. |
| 2007/0167994 A1 | 7/2007 | Shelton et al. |
| 2007/0179552 A1 | 8/2007 | Dennis et al. |
| 2007/0270675 A1 | 11/2007 | Kane et al. |
| 2007/0276004 A1 | 11/2007 | Hirsch et al. |
| 2007/0276444 A1 | 11/2007 | Gelbart et al. |
| 2007/0293904 A1 | 12/2007 | Gelbart et al. |
| 2008/0004535 A1 | 1/2008 | Smits |
| 2008/0021532 A1 | 1/2008 | Kveen et al. |
| 2008/0039738 A1 | 2/2008 | Dinsmoor et al. |
| 2008/0086168 A1 | 4/2008 | Cahill |
| 2008/0091255 A1 | 4/2008 | Caparso et al. |
| 2008/0119911 A1 | 5/2008 | Rosero |
| 2008/0243218 A1 | 10/2008 | Bottomley et al. |
| 2008/0269591 A1 | 10/2008 | Halperin et al. |
| 2009/0018599 A1 | 1/2009 | Hastings et al. |
| 2009/0082827 A1 | 3/2009 | Kveen et al. |
| 2009/0082828 A1 | 3/2009 | Ostroff |
| 2009/0149902 A1 | 6/2009 | Kumar et al. |
| 2009/0171408 A1 | 7/2009 | Solem |
| 2010/0069983 A1 | 3/2010 | Peacock et al. |
| 2010/0198288 A1 | 8/2010 | Ostroff |
| 2010/0249828 A1 | 9/2010 | Mavani et al. |
| 2010/0292541 A1 | 11/2010 | Hashiba et al. |
| 2010/0305653 A1 | 12/2010 | Lund et al. |
| 2010/0305656 A1 | 12/2010 | Imran et al. |
| 2010/0312332 A1 | 12/2010 | Forster et al. |
| 2011/0004117 A1 | 1/2011 | Neville et al. |
| 2011/0071586 A1 | 3/2011 | Jacobson |
| 2011/0077708 A1 | 3/2011 | Ostroff |
| 2011/0208260 A1 | 8/2011 | Jacobson |
| 2011/0218587 A1 | 9/2011 | Jacobson |
| 2011/0282423 A1 | 11/2011 | Jacobson |
| 2013/0041422 A1 | 2/2013 | Jacobson |
| 2013/0103109 A1 | 4/2013 | Jacobson |
| 2013/0123875 A1 | 5/2013 | Varady et al. |

FOREIGN PATENT DOCUMENTS

| | | |
|---|---|---|
| JP | H04-506167 A | 10/1992 |
| JP | 05-24521 | 9/1993 |
| JP | 06/507096 | 3/2006 |
| JP | 06/516449 | 7/2006 |
| JP | 2006-526483 A | 11/2006 |
| WO | WO93/12714 A1 | 7/1993 |
| WO | WO 98/37926 A1 | 9/1998 |
| WO | WO02/34333 A2 | 5/2002 |
| WO | WO2004/012811 | 2/2004 |
| WO | WO 2006/065394 A1 | 6/2006 |
| WO | 2007/047681 A2 | 4/2007 |
| WO | WO 2007/047681 A2 | 4/2007 |
| WO | 2007/059386 A2 | 5/2007 |
| WO | WO 2007/059386 A2 | 5/2007 |
| WO | 2008/058265 A2 | 5/2008 |

OTHER PUBLICATIONS

Beeby et al.; Micromachined silicon generator for harvesting power from vibrations; (Proceedings) PowerMEMS 2004; Kyoto, Japan; pp. 104-107; Nov. 28-30, 2004.

(56) References Cited

OTHER PUBLICATIONS

Bordacher et al.; Impact and prevention of far-field sensing in fallback mode switches; PACE; vol. 26 (pt. II); pp. 206-209; 2003.
Brandt et al.; Far-field QRS complex sensing: prevalence and timing with bipolar atrial leads; PACE; vol. 23; pp. 315-320; 2000.
Brown, Eric S.; The atomic battery; Technology Review: Published by MIT; 4 pgs.; Jun. 16, 2005.
Irnich et al.; Do we need pacemakers resistant to magnetic resonance imaging; Europace; vol. 7; pp. 353-365; 2005.
Irnich; Electronic security systems and active implantable medical devices; Journal of PACE; vol. 25; No. 8; pp. 1235-1258; Aug. 2002.
Luechinger et al.; Force and torque effects of a 1.5-tesla MRI scanner of cardiac pacemakers and ICDs; Journal of PACE; vol. 24; No. 2; pp. 199-205; Feb. 2001.
Luechinger et al.; In vivo heating of pacemaker leads during magnetic resonance imaging; European Heart Journal; vol. 26; pp. 376-383; 2005.
Lüchinger ; Safety aspects of cardiac pacemakers in magnetic resonance imaging; Dissertation submitted to the Swiss Federal Institute of Technology Zurich; 2002.
Nyenhuis et al.; MRI and Implanted Medical Devices: Basic Interactions with an emphasis on heating; vol. 5; No. 3; pp. 467-480; Sep. 2005.
Shellock et al.; Cardiac pacemaker: In vitro assessment at 1.5 T; Am Heart J; vol. 151; pp. 436-443; 2006.
Jacobson, Peter M.; U.S. Appl. No. 13/109,728 entitled "Programmer for Biostimulator System," filed May 17, 2011.
Khairkhahan et al.; U.S. Appl. No. 13/272,074 entitled "Delivery catheter systems and methods," filed Oct. 12, 2011.
Khairkhahan et al.; U.S. Appl. No. 13/272,082 entitled "Leadless cardiac pacemaker with anti-unscrewing feature," filed Oct. 12, 2011.
Ostroff, Alan; U.S. Appl. No. 13/272,092 entitled "Temperature sensor for a leadless cardiac pacemaker," filed Oct. 12, 2011.
Khairkhaha et al.; U.S. Appl. No. 13/324,781 entitled "Delivery Catheter Systems and Methods," filed Dec. 13, 2011.
Jacobson et al.; U.S. Appl. No. 13/277,151 entitled "Leadless cardiac pacemaker with conducted communication," filed Oct. 19, 2011.
Khairkhahan et al.; U.S. Appl. No. 13/324,802 entitled "Pacemaker Retrieval Systems and Methods ," filed Dec. 13, 2011.
Khairkhahan et al.; U.S. Appl. No. 13/331,922 entitled "Leadless Pacemaker with Radial Fixation Mechanism ," filed Dec. 20, 2011.
Reply Brief, U.S. Appl. No. 12/953,282, filed Oct. 29, 2012, 4 pages.
Examiner's Answer to Appeal Brief, U.S. Appl. No. 12/953,282, mailed Aug. 30, 2012, 6 pages.
Appeal Brief, U.S. Appl. No. 12/953,282, filed Jul. 13, 2012, 4 pages.
Final Office Action, U.S. Appl. No. 12/953,282, mailed Feb. 23, 2012, 12 pages.
Response to Office Action, U.S. Appl. No. 12/953,282, filed Dec. 22, 2011, 9 pages.
Non-Final Office Action, U.S. Appl. No. 12/953,282, mailed Jun. 7, 2011, 12 pages.
Notice of Allowance, U.S. Appl. No. 11/549,605, mailed Feb. 22, 2011, 4 pages.
Notice of Allowance, U.S. Appl. No. 11/549,605, mailed Jan. 5, 2011, 4 pages.
Non-Final Office Action, U.S. Appl. No. 11/549,605, mailed May 11, 2010, 16 pages.
Non-Final Office Action, U.S. Appl. No. 11/549,605, mailed Feb. 4, 2009, 13 pages.
Notice of Allowance, U.S. Appl. No. 13/109,728, mailed Jun. 25, 2012, 7 pages.
Non-Final Office Action, U.S. Appl. No. 13/109,728, mailed Dec. 1, 2011 16 pages.
Appeal Brief, U.S. Appl. No. 11/549,581, filed Mar. 7, 2013, 25 pages.
Final Office Action, U.S. Appl. No. 11/549,581, filed Oct. 16, 2012, 28 pages.
Non-Final Office Action, U.S. Appl. No. 11/549,581, filed Jun. 22, 2012, 27 pages.
Notice of Allowance, U.S. Appl. No. 11/549,599, mailed Jan. 23, 2013, 7 pages.
Non-Final Office Action, U.S. Appl. No. 11/549,599, mailed Aug. 26, 2012, 12 pages.
Non-Final Office Action, U.S. Appl. No. 11/549,599, mailed May 4, 2012, 40 pages.
Final Office Action, U.S. Appl. No. 11/549,599, mailed Aug. 30, 2010, 10 pages.
Non-Final Office Action, U.S. Appl. No. 11/549,599, mailed Mar. 17, 2010, 9 pages.
Final Office Action, U.S. Appl. No. 11/549,599, mailed Nov. 25, 2009, 14 pages.
Non-Final Office Action, U.S. Appl. No. 11/549,599, mailed Dec. 9, 2008, 35 pages.
Notice of Allowance, U.S. Appl. No. 11/549,596, mailed Sep. 10, 2012, 5 pages.
Non-Final Office Action, U.S. Appl. No. 11/549,596, mailed May 21, 2012, 8 pages.
Final Office Action, U.S. Appl. No. 11/549,596, mailed Aug. 31, 2010, 10 pages.
Non-Final Office Aciion, U.S. Appl. No. 11/549,596, mailed Mar. 17, 2010, 8 pages.
Final Office Action, U.S. Appl. No. 11/549,596, mailed Nov. 27, 2009, 10 pages.
Non-Final Office Action, U.S. Appl. No. 11/549,596, mailed Nov. 25, 2008, 29 pages.
Reply Brief, U.S. Appl. No. 11/549,591, filed May 8, 2012, 4 pages.
Examiner's Answer, U.S. Appl. No. 11/549,591, mailed Mar. 13, 2012, 12 pages.
Appeal Brief, U.S. Appl. No. 11/549,591, filed Oct. 10, 2011, 20 pages.
Final Office Action, U.S. Appl. No. 11/549,591, mailed Apr. 27, 2011, 11 pages.
Non-Final Office Action, U.S. Appl. No. 11/549,591, mailed Nov. 24, 2010, 10 pages.
Non-Final Office Action, U.S. Appl. No. 11/549,591, mailed May 12, 2010, 11 pages.
Non-Final Office Action, U.S. Appl. No. 11/549,591, mailed Dec. 9, 2008, 35 pages.
Notice of Allowance, U.S. Appl. No. 13/277,151, mailed Sep. 25, 2014, 10 pages.
Terminal Disclaimer, U.S. Appl. No. 13/277,151, filed Sep. 12, 2014, 2 pages.
Advisory Action, U.S. Appl. No. 13/277,151, mailed Aug. 14, 2014, 5 pages.
Final Office Action, U.S. Appl. No. 13/277,151, mailed Jun. 24, 2014, 22 pages.
Non-Final Office Action, U.S. Appl. No. 13/277,151, mailed Sep. 11, 2013, 18 pages.
European Patent Office, "Communication of a Notice of Opposition," European Application No. 06836350.6, Oct. 24, 2014, 35 pages.
Design of cardiac pacemakers, edited by J.G. Webster, 1995, Chapter 11.
International Searching Authority, "Notification of Transmittal of the International Search Report and the Written Opinion of the International Searching Authority, or the Declaration," International Application No. PCT/US12/57776, Jan. 10, 2013, 12 pages.
International Searching Authority, "Notification of Transmittal of the International Search Report and the Written Opinion of the International Searching Authority, or the Declaration," International Application No. PCT/US06/40564, Apr. 8, 2008, 29 pages.
Jacobson, Peter M.; U.S. Appl. No. 13/708,732 entitled "Leadless cardiac pacemaker Triggered by Conductive Communication," filed Dec. 7, 2012.
Ostroff et al.; U.S. Appl. No. 13/910,896 entitled "Leadless Pacemaker with Multiple Electrodes," filed Jun. 5, 2013.
Varady et al.; U.S. Appl. No. 13/669,242 entitled "Leadless Cardiac Pacemaker with Integral Battery and Redundant Welds," filed Nov. 5, 2012.

* cited by examiner

RATE RESPONSIVE LEADLESS CARDIAC PACEMAKER

CROSS REFERENCE TO RELATED APPLICATIONS

This application is a continuation of U.S. patent application Ser. No. 11/549,603, filed Oct. 13, 2006, now U.S. Pat. No. 7,937,148; which application claims the benefit of priority to and incorporates herein by reference in its entirety for all purposes, U.S. Provisional Application Nos. 60/726,706, entitled "LEADLESS CARDIAC PACEMAKER WITH CONDUCTED COMMUNICATION," filed Oct. 14, 2005; 60/761,531, entitled "LEADLESS CARDIAC PACEMAKER DELIVERY SYSTEM," filed Jan. 24, 2006; 60/729,671, entitled "LEADLESS CARDIAC PACEMAKER TRIGGERED BY CONDUCTED COMMUNICATION," filed Oct. 24, 2005; 60/737,296, entitled "SYSTEM OF LEADLESS CARDIAC PACEMAKERS WITH CONDUCTED COMMUNICATION," filed Nov. 16, 2005; 60/739,901, entitled "LEADLESS CARDIAC PACEMAKERS WITH CONDUCTED COMMUNICATION FOR USE WITH AN IMPLANTABLE CARDIOVERTER-DEFIBRILLATOR," filed Nov. 26, 2005; 60/749,017, entitled "LEADLESS CARDIAC PACEMAKER WITH CONDUCTED COMMUNICATION AND RATE RESPONSIVE PACING," filed Dec. 10, 2005; and 60/761,740, entitled "PROGRAMMER FOR A SYSTEM OF LEADLESS CARDIAC PACEMAKERS WITH CONDUCTED COMMUNICATION," filed Jan. 24, 2006; all by Peter M. Jacobson.

BACKGROUND

Cardiac pacing electrically stimulates the heart when the heart's natural pacemaker and/or conduction system fails to provide synchronized atrial and ventricular contractions at appropriate rates and intervals for a patient's needs. Such bradycardia pacing provides relief from symptoms and even life support for hundreds of thousands of patients. Cardiac pacing may also give electrical overdrive stimulation intended to suppress or convert tachyarrhythmias, again supplying relief from symptoms and preventing or terminating arrhythmias that could lead to sudden cardiac death.

Cardiac pacing is usually performed by a pulse generator implanted subcutaneously or sub-muscularly in or near a patient's pectoral region. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Known pulse generators can include various sensors for estimating metabolic demand, to enable an increase in pacing rate proportional and appropriate for the level of exercise. The function is usually known as rate-responsive pacing. For example, an accelerometer can measure body motion and indicate activity level. A pressure transducer in the heart can sense the timing between opening and closing of various cardiac valves, or can give a measure of intracardiac pressure directly, both of which change with changing stroke volume. Stroke volume increases with increased activity level. A temperature sensor can detect changes in a patient's blood temperature, which varies based on activity level. The pacemaker can increase rate proportional to a detected increase in activity.

Pulse generator parameters are usually interrogated and modified by a programming device outside the body, via a loosely-coupled transformer with one inductance within the body and another outside, or via electromagnetic radiation with one antenna within the body and another outside.

Although more than one hundred thousand rate-responsive pacemakers are implanted annually, various well-known difficulties are present.

The pulse generator, when located subcutaneously, presents a bulge in the skin that patients can find unsightly or unpleasant. Patients can manipulate or "twiddle" the device. Even without persistent twiddling, subcutaneous pulse generators can exhibit erosion, extrusion, infection, and disconnection, insulation damage, or conductor breakage at the wire leads. Although sub-muscular or abdominal placement can address some of concerns, such placement involves a more difficult surgical procedure for implantation and adjustment, which can prolong patient recovery.

A conventional pulse generator, whether pectoral or abdominal, has an interface for connection to and disconnection from the electrode leads that carry signals to and from the heart. Usually at least one male connector molding has at least one terminal pin at the proximal end of the electrode lead. The at least one male connector mates with at least one corresponding female connector molding and terminal block within the connector molding at the pulse generator. Usually a setscrew is threaded in at least one terminal block per electrode lead to secure the connection electrically and mechanically. One or more O-rings usually are also supplied to help maintain electrical isolation between the connector moldings. A setscrew cap or slotted cover is typically included to provide electrical insulation of the setscrew. The complex connection between connectors and leads provides multiple opportunities for malfunction.

For example, failure to introduce the lead pin completely into the terminal block can prevent proper connection between the generator and electrode.

Failure to insert a screwdriver correctly through the setscrew slot, causing damage to the slot and subsequent insulation failure.

Failure to engage the screwdriver correctly in the setscrew can cause damage to the setscrew and preventing proper connection.

Failure to tighten the setscrew adequately also can prevent proper connection between the generator and electrode, however over-tightening of the setscrew can cause damage to the setscrew, terminal block, or lead pin, and prevent disconnection if necessary for maintenance.

Fluid leakage between the lead and generator connector moldings, or at the setscrew cover, can prevent proper electrical isolation.

Insulation or conductor breakage at a mechanical stress concentration point where the lead leaves the generator can also cause failure.

Inadvertent mechanical damage to the attachment of the connector molding to the generator can result in leakage or even detachment of the molding.

Inadvertent mechanical damage to the attachment of the connector molding to the lead body, or of the terminal pin to the lead conductor, can result in leakage, an open-circuit condition, or even detachment of the terminal pin and/or molding.

The lead body can be cut inadvertently during surgery by a tool, or cut after surgery by repeated stress on a ligature used to hold the lead body in position. Repeated movement for hundreds of millions of cardiac cycles can cause lead conductor breakage or insulation damage anywhere along the lead body.

Although leads are available commercially in various lengths, in some conditions excess lead length in a patient exists and is to be managed. Usually the excess lead is coiled near the pulse generator. Repeated abrasion between the lead body and the generator due to lead coiling can result in insulation damage to the lead.

Friction of the lead against the clavicle and the first rib, known as subclavian crush, can result in damage to the lead.

In many applications, such as dual-chamber pacing, multiple leads can be implanted in the same patient and sometimes in the same vessel. Abrasion between the leads for hundreds of millions of cardiac cycles can cause insulation breakdown or even conductor failure.

Communication between the implanted pulse generator and external programmer uses a telemetry coil or antenna and associated circuitry in the pulse generator, adding complexity that increases the size and cost of devices. Moreover, power consumption from the pulse generator battery for communication typically exceeds power for pacing by one or more orders of magnitude, introducing a requirement for battery power capability that can prevent selecting the most optimal battery construction for the otherwise low-power requirements of pacing.

SUMMARY

According to an embodiment of a biostimulation system, a leadless cardiac pacemaker comprises a housing, a plurality of electrodes coupled to an outer surface of the housing, and a pulse delivery system hermetically contained within the housing and electrically coupled to the electrode plurality, the pulse delivery system configured for sourcing energy internal to the housing, generating and delivering electrical pulses to the electrode plurality. The pacemaker further comprises an activity sensor hermetically contained within the housing and adapted to sense activity and a processor hermetically contained within the housing and communicatively coupled to the pulse delivery system, the activity sensor, and the electrode plurality, the processor configured to control electrical pulse delivery at least partly based on the sensed activity.

BRIEF DESCRIPTION OF THE DRAWINGS

Embodiments of the invention relating to both structure and method of operation may best be understood by referring to the following description and accompanying drawings, in which similar reference characters denote similar elements throughout the several views.

DETAILED DESCRIPTION

In an illustrative system, a rate-responsive leadless cardiac pacemaker can be implanted adjacent to the inside or outside wall of a cardiac chamber.

In addition, a technique for rate-responsive pacing enables pacing control of the leadless cardiac pacemaker which is implanted adjacent to the inside or outside wall of a cardiac chamber.

A cardiac pacemaker for implantation in the human body, more specifically a leadless cardiac pacemaker for implantation adjacent to the inside or outside wall of a cardiac chamber, uses two or more electrodes located within, on, or within two centimeters of the housing of the pacemaker for pacing and sensing at the cardiac chamber and for bidirectional communication with at least one other device within or outside the body. The pacemaker contains an activity sensor, such as an accelerometer, temperature sensor, and/or a pressure transducer to measure patient activity, enabling rate-responsive pacing.

The illustrative system enables cardiac pacing without a pulse generator located in the pectoral region or abdomen, without an electrode-lead separate from the pulse generator, without a communication coil or antenna, and without an additional requirement on battery power for transmitted communication.

An illustrative rate-responsive leadless cardiac pacemaker can be substantially enclosed in a hermetic housing suitable for placement on or attachment to the inside or outside of a cardiac chamber. The pacemaker has at least two electrodes located within, on, or near the housing, for delivering pacing pulses to and sensing electrical activity from the muscle of the cardiac chamber, and for bidirectional communication with at least one other device within or outside the body. The housing contains a primary battery to provide power for pacing, sensing, and communication. The housing also contains circuits for sensing cardiac activity from the electrodes, receiving information from at least one other device via the electrodes, generating pacing pulses for delivery via the electrodes, transmitting information to at least one other device via the electrodes, monitoring device health, and controlling these operations in a predetermined manner.

A leadless pacemaker is configured for implantation adjacent to the inside or outside wall of a cardiac chamber, without the need for a connection between the pulse generator and electrode lead, and without the need for a lead body.

In some embodiments, the illustrative system enables communication between the implanted pulse generator and a device internal or external to the body, using conducted communication via the same electrodes used for pacing, without the need for an antenna or telemetry coil.

Still other embodiments enable communication between the implanted pulse generator and a device internal or external to the body, with power consumption similar to that for cardiac pacing, to allow optimization of battery performance.

Figure 1A:
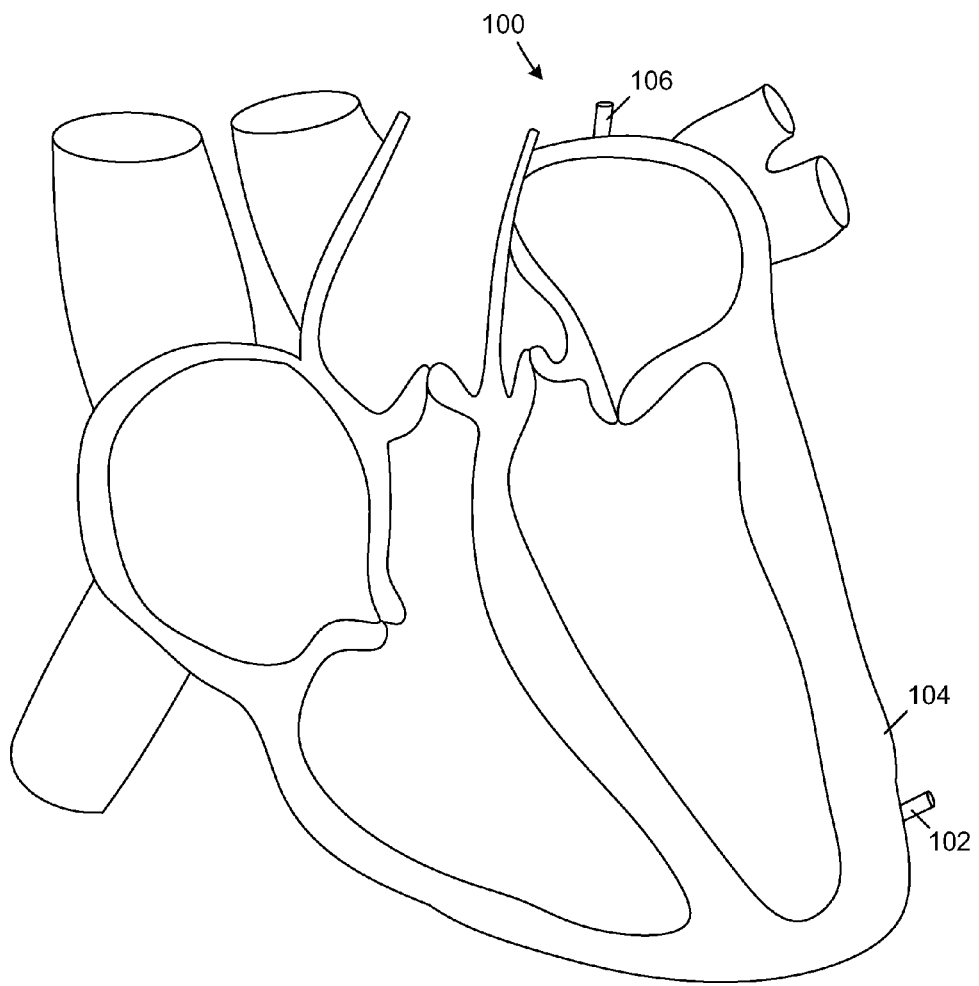
FIG. 1A is a pictorial diagram showing an embodiment of a cardiac pacing system that includes a rate-responsive leadless cardiac pacemaker.
Figure 1B:
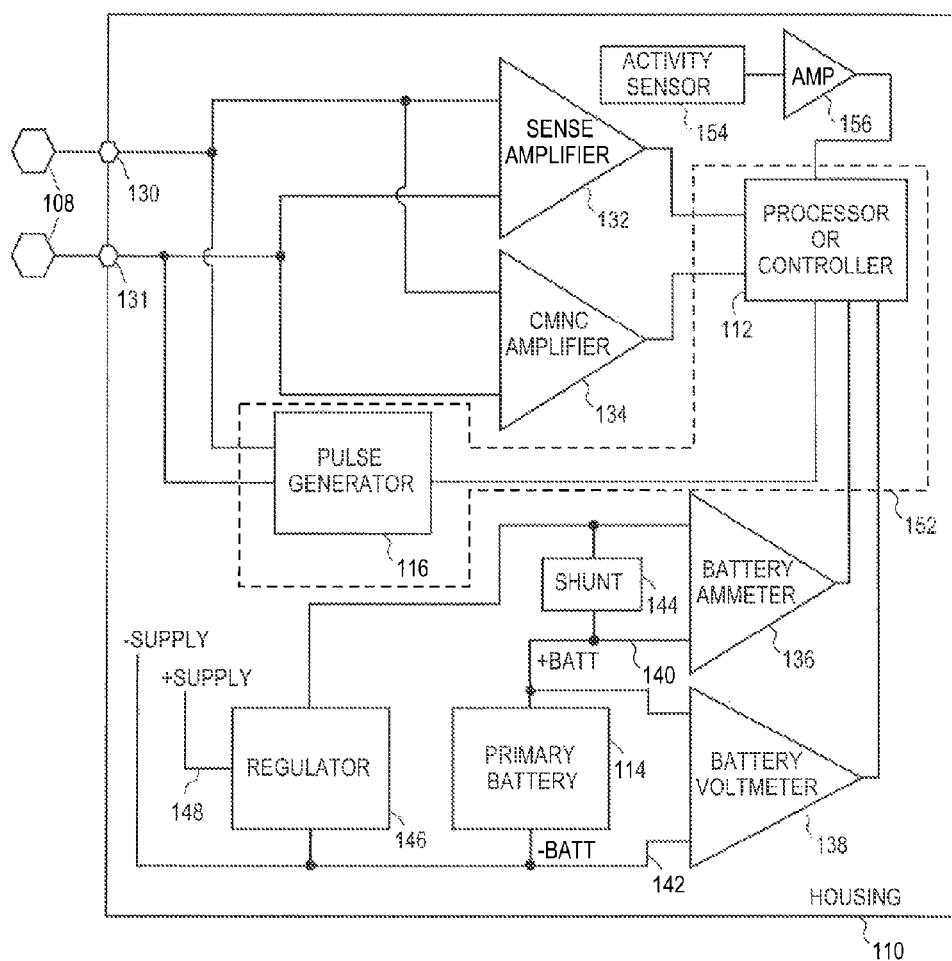
FIG. 1B is a schematic block diagram showing interconnection of operating elements of an embodiment of the illustrative rate-responsive leadless cardiac pacemaker.

Referring to FIGS. 1A and 1B, a pictorial view which is not shown to scale and a schematic block diagram respectively depict an embodiment of a cardiac pacing system 100 that comprises a rate-responsive leadless cardiac pacemaker 102. The rate-responsive leadless cardiac pacemaker 102 comprises a housing 110, multiple electrodes 108 coupled to the housing 110, a pulse delivery system 152 hermetically contained within the housing 110 and electrically coupled to the electrodes 108. The pulse delivery system 152 configured for sourcing energy internal to the housing 110, generating and delivering electrical pulses to the electrodes 108. The rate-responsive leadless cardiac pacemaker 102 further comprises an activity sensor 154 which is hermetically contained within the housing 110 and adapted to sense activity. A processor 112 is also hermetically contained within the housing 110 as part of a pulse delivery system 152 and is communicatively coupled to the activity sensor 154, and the electrodes 108. The processor 112 can control electrical pulse delivery at least partly based on the sensed activity.

In various embodiments, the electrodes 108 can be coupled on, within, or within two centimeters of the housing 110. In some arrangements, the electrodes 108 can be formed integrally to an outer surface of the housing 110.

Referring to FIG. 1B, the rate-responsive leadless cardiac pacemaker 102 has functional elements substantially enclosed in a hermetic housing 110. The pacemaker has at least two electrodes 108 located within, on, or near the housing 110, for delivering pacing pulses to and sensing electrical activity from the muscle of the cardiac chamber, and for bidirectional communication with at least one other device within or outside the body. Hermetic feedthroughs 130, 131 conduct electrode signals through the housing 110. The housing 110 contains a primary battery 114 to provide power for pacing, sensing, and communication. The housing 110 contains circuits 132 for sensing cardiac activity from the electrodes 108; circuits 134 for receiving information from at least one other device via the electrodes 108; and a pulse generator 116 for generating pacing pulses for delivery via the electrodes 108 and also for transmitting information to at least one other device via the electrodes 108. The pacemaker 102 further contains circuits for monitoring device health, for example a battery current monitor 136 and a battery voltage monitor 138. The pacemaker 102 further contains processor or controller circuits 112 for controlling these operations in a predetermined manner.

In accordance with another embodiment of a pacing system, a leadless cardiac pacemaker 102 comprises a housing 110, multiple electrodes 108 coupled to the housing 108, and a pulse generator 116 hermetically contained within the housing 110 and electrically coupled to the electrodes 108. The pulse generator 116 is configured to generate and deliver electrical pulses to the electrodes 108 powered from a source 114 contained entirely within the housing 110. An activity sensor 154 is hermetically contained within the housing 110 and adapted to sense activity. A logic 112, for example a processor, controller, central processing unit, state machine, programmable logic array, and the like, which is hermetically contained within the housing 110 and communicatively coupled to the pulse generator 116, the activity sensor 154, and the electrodes 108. The logic 112 is configured to control electrical pulse delivery at least partly based on the sensed activity.

In some embodiments, the logic 112 can be a processor that controls electrical pulse delivery and application of the activity sensor according to one or more programmable parameters with the processor programmable by communication signals transmitted via the electrodes 108.

The information communicated on the incoming communication channel can include, but is not limited to pacing rate, pulse duration, sensing threshold, and other parameters commonly programmed externally in typical pacemakers. The information communicated on the outgoing communication channel can include, but is not limited to programmable parameter settings, event counts (pacing and sensing), battery voltage, battery current, and other information commonly displayed by external programmers used with common pacemakers. The outgoing communication channel can also echo information from the incoming channel, to confirm correct programming.

Also shown in FIG. 1B, the primary battery 114 has positive terminal 140 and negative terminal 142. A suitable primary battery has an energy density of at least 3 W·h/cc, a power output of 70 microwatts, a volume less than 1 cubic centimeter, and a lifetime greater than 5 years.

One suitable primary battery uses beta-voltaic technology, licensed to BetaBatt Inc. of Houston, Tex., USA, and developed under a trade name DEC™ Cell, in which a silicon wafer captures electrons emitted by a radioactive gas such as tritium. The wafer is etched in a three-dimensional surface to capture more electrons. The battery is sealed in a hermetic package which entirely contains the low-energy particles emitted by tritium, rendering the battery safe for long-term human implant from a radiological-health standpoint. Tritium has a half-life of 12.3 years so that the technology is more than adequate to meet a design goal of a lifetime exceeding 5 years.

In accordance with another embodiment of a pacing system, a leadless cardiac pacemaker 102 comprises a housing 110, multiple electrodes 108 coupled to the housing 110, and a pulse generator 116 hermetically contained within the housing 110 and electrically coupled to the electrodes 108. The pulse generator 116 generates and delivers electrical pulses to the electrodes 108, causing cardiac contractions. The pulse generator 116 also conveys information to one or more devices 106 external to the pacemaker 102. The pacemaker 102 further comprises at least one amplifier 132, 134 hermetically contained within the housing 110 and electrically coupled to the electrodes 108. The amplifier or amplifiers 132, 134 are configured to amplify signals received from the electrodes 108 and to detect cardiac contractions, and further can receive information from the external device or devices 106. The pacemaker 102 further comprises a power supply 114 hermetically contained within the housing 110 and coupled to the pulse generator 116. The power supply 114 sources energy for the electrical pulses from internal to the housing 110. The pacemaker 102 has an activity sensor 154 hermetically contained within the housing 110 that senses activity. A processor 112 is hermetically contained within the housing 110 and communicatively coupled to the pulse generator 116, the amplifiers 132, 134, the activity sensor 154, and the electrodes 108. The processor 112 configured to receive amplifier output signals from the amplifier or amplifiers 132, 134 and control electrical pulse delivery at least partly based on the sensed activity.

In an illustrative embodiment, the amplifiers comprise a cardiac sensing amplifier 132 that consumes no more than 5 microwatts, a communications amplifier 134 that consumes no more than 25 microwatts, and a rate-response sensor amplifier 156 that consumes no more than 10 microwatts.

In an example embodiment, the regulator 146 can be configured to consume electrical power of no more than 2 microwatts and configured to supply electrical power of no more than 74 microwatts in the illustrative system that includes a rate-response amplifier.

The processor 112 can be configured to consume electrical power of no more than 5 microwatts averaged over one cardiac cycle.

Current from the positive terminal 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the processor 112 with an indication of battery current drain and indirectly of device health.

The illustrative power supply can be a primary battery 114 such as a beta-voltaic converter that obtains electrical energy from radioactivity. In some embodiments, the power supply can be selected as a primary battery 114 that has a volume less than approximately 1 cubic centimeter.

In an illustrative embodiment, the primary battery 114 can be selected to source no more than 75-80 microwatts instantaneously since a higher consumption may cause the voltage across the battery terminals to collapse. Accordingly in one illustrative embodiment the circuits depicted in FIG. 1B can be designed to consume no more than a total of 74 microwatts. The design avoids usage of a large filtering capacitor for the power supply or other accumulators such as a supercapacitor or rechargeable secondary cell to supply peak power exceeding the maximum instantaneous power capability of the battery, components that would add volume and cost.

In various embodiments, the system can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

Implantable systems that communicate via long distance radio-frequency (RF) schemes, for example Medical Implant Communication Service (MICS) transceivers, which exhibit a peak power requirement on the order of 10 milliwatts, and other RF or inductive telemetry schemes are unable to operate without use of an additional accumulator. Moreover, even with the added accumulator, sustained operation would ultimately cause the voltage across the battery to collapse.

In various embodiments, the activity sensor 154 is adapted for controlling rate-responsive pacing and may use any appropriate technology, for the example the activity sensor 154 may be an accelerometer, a temperature sensor, a pressure sensor, or any other suitable sensor.

In an illustrative embodiment, the activity sensor 154 can operate with a power requirement of no more than 10 microwatts.

FIG. 1B shows a pacemaker embodiment wherein the activity sensor comprises an accelerometer 154 and an accelerometer amplifier 156 configured to detect patient activity for rate-responsive pacing. The accelerometer amplifier output terminal is connected to the processor 112. Because the leadless cardiac pacemaker 102 is attached to cardiac muscle 104, the accelerometer 154 measures some acceleration due to heartbeats in addition to the desired activity signal. Processor 112 performs sampling of the accelerometer output signal synchronously with the cardiac cycle as determined by the cardiac sensing amplifier 132 and the pulse generator 116. Processor 112 then compares acceleration signals taken at the same relative time in multiple cardiac cycles to distinguish the part of the acceleration signal that results from activity and is not due to heart wall motion.

In other embodiments, the accelerometer 154 and accelerometer amplifier 156 shown in FIG. 1B can be replaced with a temperature transducer such as a thermistor and a signal conditioning amplifier connected to processor 112. In another embodiment, a pressure transducer and signal conditioning amplifier can be connected to processor 112. Temperature is not sensitive to the cardiac cycle so that in such an activity sensor rate-responsive cardiac pacemaker embodiments, synchronous sampling with the cardiac cycle is superfluous. Although pressure varies in the cardiac cycle, easily measured features of the pressure wave, for example peak amplitude, peak-to-peak amplitude, peak rate of change (delta), and the like, can indicate the level of activity.

Figure 2:
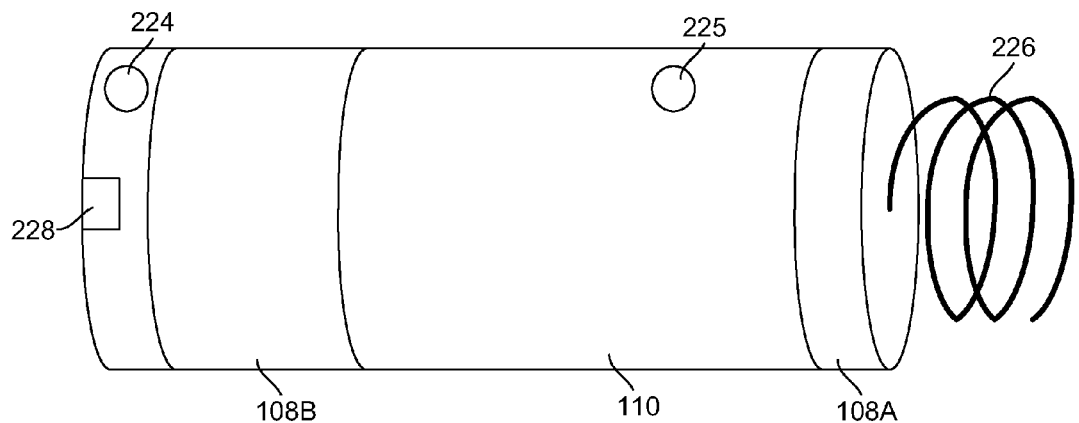
FIG. 2 is a pictorial diagram showing the physical location of some elements of an embodiment of a rate-responsive leadless cardiac pacemaker.

Also shown in FIG. 2, a cylindrical hermetic housing 110 is shown with annular electrodes 108 at housing extremities. In the illustrative embodiment, the housing 110 can be composed of alumina ceramic which provides insulation between the electrodes. The electrodes 108 are deposited on the ceramic, and are platinum or platinum-iridium.

Several techniques and structures can be used for attaching the housing 110 to the interior or exterior wall of cardiac muscle 104.

A helix 226 and slot 228 enable insertion of the device endocardially or epicardially through a guiding catheter. A screwdriver stylet can be used to rotate the housing 110 and force the helix 226 into muscle 104, thus affixing the electrode 108A in contact with stimulable tissue. Electrode 108B serves as an indifferent electrode for sensing and pacing. The helix 226 may be coated for electrical insulation, and a steroid-eluting matrix may be included near the helix to minimize fibrotic reaction, as is known in conventional pacing electrode-leads.

In other configurations, suture holes 224 and 225 can be used to affix the device directly to cardiac muscle with ligatures, during procedures where the exterior surface of the heart can be accessed.

The leadless cardiac pacemaker or pacemakers 102 can be configured to detect a natural cardiac depolarization, time a selected delay interval, and deliver an information-encoded pulse during a refractory period following the natural cardiac depolarization. By encoding information in a pacing pulse, power consumed for transmitting information is not significantly greater than the power used for pacing. Information can be transmitted through the communication channel with no separate antenna or telemetry coil. Communication bandwidth is low with only a small number of bits encoded on each pulse.

In some embodiments, information can be encoded using a technique of gating the pacing pulse for very short periods of time at specific points in the pacing pulse. During the gated sections of the pulse, no current flows through the electrodes of a leadless cardiac pacemaker. Timing of the gated sections can be used to encode information. The specific length of a gated segment depends on the programmer's ability to detect the gated section. A certain amount of smoothing or low-pass filtering of the signal can be expected from capacitance inherent in the electrode/skin interface of the programmer as well as the electrode/tissue interface of the leadless cardiac pacemaker. A gated segment is set sufficiently long in duration to enable accurate detection by the programmer, limiting the amount of information that can be transmitted during a single pacing pulse. Accordingly, a technique for communication can comprise generating stimulation pulses on stimulating electrodes of an implanted biostimulator and encoding information onto generated stimulation pulses. Encoding information onto the pulses can comprise gating the stimulation pulses for selected durations at selected timed sections in the stimulation pulses whereby gating removes current flow through the stimulating electrodes and timing of the gated sections encodes the information.

Another method of encoding information on pacing pulses involves varying the timing between consecutive pacing pulses in a pulse sequence. Pacing pulses, unless inhibited or triggered, occur at predetermined intervals. The interval between any two pulses can be varied slightly to impart information on the pulse series. The amount of information, in bits, is determined by the time resolution of the pulse shift. The steps of pulse shifting are generally on the order of microseconds. Shifting pulses by up to several milliseconds does not have an effect on the pacing therapy and cannot be sensed by the patient, yet significant information can be transmitted by varying pulse intervals within the microsecond range. The method of encoding information in variation of pulses is less effective if many of the pulses are inhibited or triggered. Accordingly, a technique for communication can comprise generating stimulation pulses on stimulating electrodes of an implanted biostimulator and encoding information onto generated stimulation pulses comprising selectively varying timing between consecutive stimulation pulses.

Alternatively or in addition to encoding information in gated sections and/or pulse interval, overall pacing pulse width can be used to encode information.

The three described methods of encoding information on pacing pulses can use the programmer to distinguish pacing pulses from the patient's normal electrocardiogram, for example by recognition of the specific morphology of the pacing pulse compared to the R-wave generated during the cardiac cycle. For example, the external programmer can be adapted to distinguish a generated cardiac pacing pulse from a natural cardiac depolarization in an electrocardiogram by performing comparative pattern recognition of a pacing pulse an an R-wave produced during a cardiac cycle.

Other attachment structures used with conventional cardiac electrode-leads including tines or barbs for grasping trabeculae in the interior of the ventricle, atrium, or coronary sinus may also be used in conjunction with or instead of the illustrative attachment structures.

Figure 3:
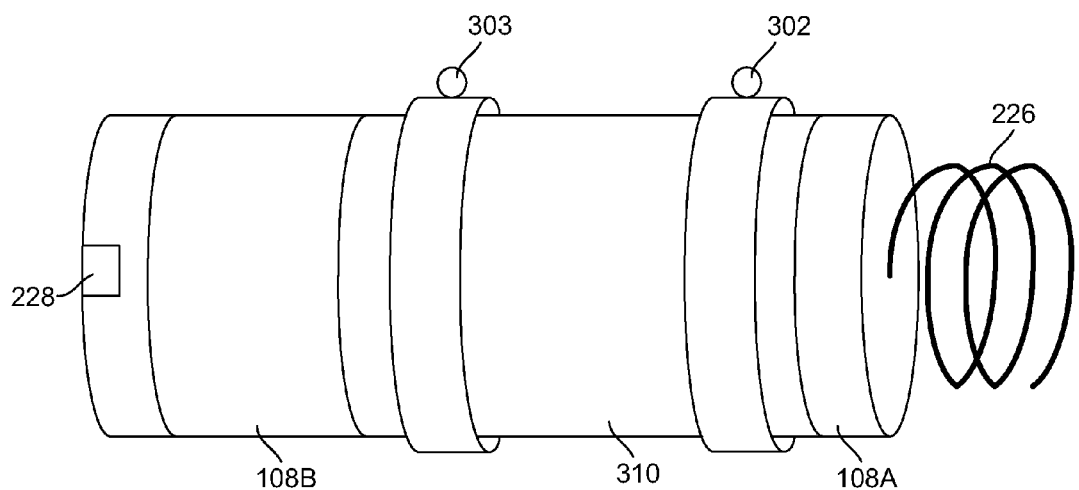
FIG. 3 is a pictorial diagram that depicts the physical location of some elements in an alternative embodiment of a rate-responsive leadless cardiac pacemaker.

Referring to FIG. 3, a pictorial view shows another embodiment of a pulse generator that includes a cylindrical metal housing 310 with an annular electrode 108A and a second electrode 108B. Housing 310 can be constructed from titanium or stainless steel. Electrode 108A can be constructed using a platinum or platinum-iridium wire and a ceramic or glass feed-thru to provide electrical isolation from the metal housing. The housing can be coated with a biocompatible polymer such as medical grade silicone or polyurethane except for the region outlined by electrode 108B. The distance between electrodes 108A and 108B should be selected to optimize sensing amplitudes and pacing thresholds. A helix 226 and slot 228 can be used for insertion of the device endocardially or epicardially through a guiding catheter. In addition, suture sleeves 302 and 303 made from silicone can be used to affix to the device directly to cardiac muscle with ligatures.

In accordance with another embodiment of a pacing system 100, a pacemaker configured as a rate-responsive leadless cardiac pacemaker 102 comprising a housing 110, and multiple electrodes 108 coupled to the housing 110. A pulse generator 116 hermetically contained within the housing 110 and electrically coupled to the electrodes 108 and is configured for generating and delivering electrical pulses to the electrodes 108. An activity sensor 154 is hermetically contained within the housing 110 and adapted to sense activity. A processor 112 is hermetically contained within the housing and communicatively coupled to the pulse generator 116, the activity sensor 154, and the electrodes 108. The processor 112 controls electrical pulse delivery at least partly based on the sensed activity and communicates with one or more devices 106 external to the pacemaker 102 via signals conducted through the electrodes 108.

In various embodiments, the processor 112 and pulse delivery system 152 transmits and/or receives information such as programmable parameter settings, event counts, power-supply voltage, power-supply current, rate-response control parameters adapted for converting an activity sensor signal to a rate-responsive pacing parameter.

Figure 4:
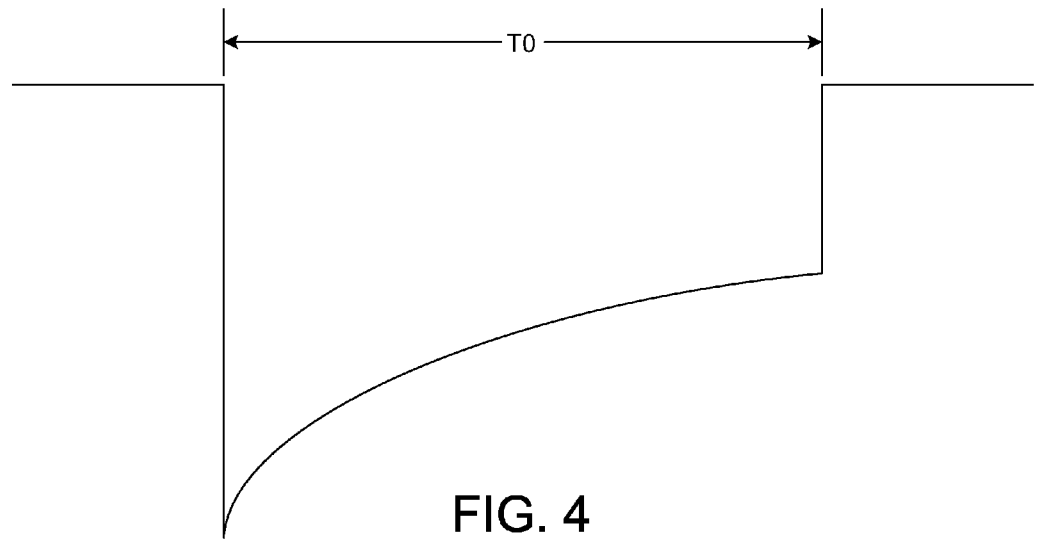
FIG. 4 is a time waveform graph illustrating a conventional pacing pulse.

Referring to FIG. 4, a typical output-pulse waveform for a conventional pacemaker is shown. The approximately-exponential decay is due to discharge of a capacitor in the pacemaker through the approximately-resistive load presented by the electrodes/tissue interface and leads. Typically the generator output is capacitor-coupled to one electrode to ensure net charge balance. The pulse duration is shown as T0 and is typically 500 microseconds.

When the pacemaker 102 is supplying a pacing pulse but is not sending data for communication, the waveform can resemble that shown in FIG. 4.

In some embodiments, configurations, or conditions, the processor 112 and pulse delivery system 152 are configured to generate and deliver electrical energy with the stimulation pulse interrupted by at least one notch that conveys information to a device 106 external to the pacemaker 102.

Figure 5:
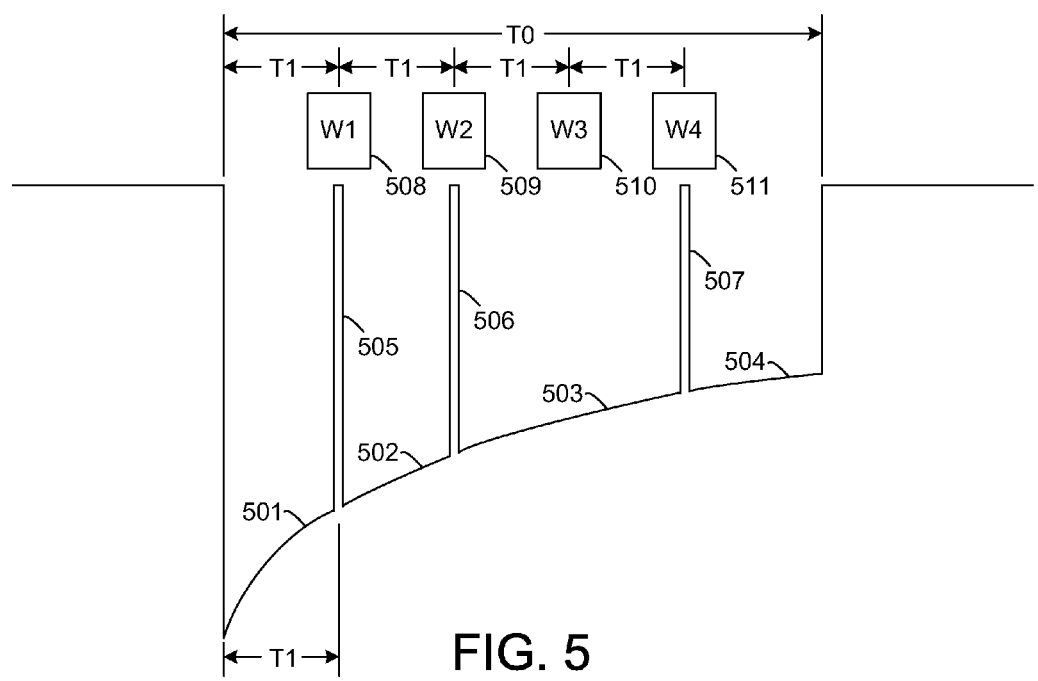
FIG. 5 is a time waveform graph depicting a pacing pulse adapted for communication as implemented for an embodiment of the illustrative pacing system.

Referring to FIG. 5, a time waveform graph depicts an embodiment of a sample output-pacing pulse waveform adapted for communication. The output-pulse waveform of the illustrative leadless pacemaker 102 is shown during a time when the pacemaker 102 is sending data for communication and also delivering a pacing pulse, using the same pulse generator 116 and electrodes 108 for both functions.

FIG. 5 shows that the pulse generator 102 has divided the output pulse into shorter pulses 501, 502, 503, 504; separated by notches 505, 506, and 507. The pulse generator 102 times the notches 505, 506, and 507 to fall in timing windows W1, W2, and W4 designated 508, 509, and 511 respectively. Note that the pacemaker 102 does not form a notch in timing window W3 designated 510. The timing windows are each shown separated by a time T1, approximately 100 microseconds in the example.

As controlled by processor 112, pulse generator 116 selectively generates or does not generate a notch in each timing window 508, 509, 510, and 511 so that the device 102 encodes four bits of information in the pacing pulse. A similar scheme with more timing windows can send more or fewer bits per pacing pulse. The width of the notches is small, for example approximately 15 microseconds, so that the delivered charge and overall pulse width, specifically the sum of the widths of the shorter pulses, in the pacing pulse is substantially unchanged from that shown in FIG. 4. Accordingly, the pulse shown in FIG. 5 can have approximately the same pacing effectiveness as that shown in FIG. 4, according to the law of Lapique which is well known in the art of electrical stimulation.

In a leadless cardiac pacemaker, a technique can be used to conserve power when detecting information carried on pacing pulses from other implanted devices. The leadless cardiac pacemaker can have a receiving amplifier that implements multiple gain settings and uses a low-gain setting for normal operation. The low-gain setting could be insufficiently sensitive to decode gated information on a pacing pulse accurately but could detect whether the pacing pulse is present. If an edge of a pacing pulse is detected during low-gain operation, the amplifier can be switched quickly to the high-gain setting, enabling the detailed encoded data to be detected and decoded accurately. Once the pacing pulse has ended, the receiving amplifier can be set back to the low-gain setting. For usage in the decoding operation, the receiving amplifier is configured to shift to the more accurate high-gain setting quickly when activated. Encoded data can be placed at the end of the pacing pulse to allow a maximum amount of time to invoke the high-gain setting.

In some embodiments, configurations, or conditions, the processor 112 and pulse delivery system 152 are configured to generate and deliver electrical energy with the stimulation pulse that conveys information to a device 106 external to the pacemaker 102 in designated codes encoding the information in modulation of off-time between pacing pulses.

Figure 6:
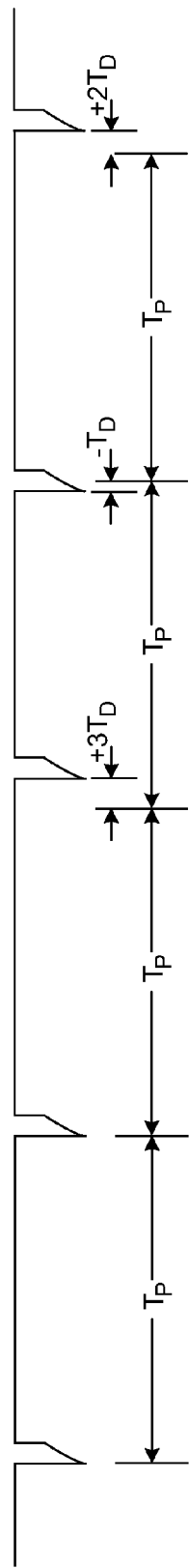
FIG. 6 is a time waveform graph showing a sample pulse waveform using off-time variation for communication.

As an alternative or in addition to using notches in the stimulation pulse, the pulses can be generated with varying off-times, specifically times between pulses during which no stimulation occurs. The variation of off-times can be small, for example less than 10 milliseconds total, and can impart information based on the difference between a specific pulse's off-time and a preprogrammed off-time based on desired heart rate. For example, the device can impart four bits of information with each pulse by defining 16 off-times centered around the preprogrammed off-time. FIG. 6 is a graph showing a sample pulse generator output which incorporates a varying off-time scheme. In the figure, time $T_P$ represents the preprogrammed pulse timing. Time $T_d$ is the delta time associated with a single bit resolution for the data sent by the pulse generator. The number of $T_d$ time increments before or after the moment specified by $T_P$ gives the specific data element transmitted. The receiver of the pulse generator's communication has advance information of the time $T_P$. The communication scheme is primarily applicable to overdrive pacing in which time $T_P$ is not changing based on detected beats.

In some embodiments, configurations, or conditions, the processor 112 and pulse delivery system 152 are configured to generate and deliver electrical energy with the stimulation pulse that conveys information to a device 106 external to the pacemaker 102 in designated codes encoding the information in pacing pulse width.

FIG. 5 depicts a technique in which information is encoded in notches in the pacing pulse. FIG. 6 shows a technique of conveying information by modulating the off-time between pacing pulses. Alternatively or in addition to the two illustrative coding schemes, overall pacing pulse width can be used to impart information. For example, a paced atrial beat may exhibit a pulse width of 500 microseconds and an intrinsic atrial contraction can be identified by reducing the pulse width by 30 microseconds. Information can be encoded by the absolute pacing pulse width or relative shift in pulse width. Variations in pacing pulse width can be relatively small and have no impact on pacing effectiveness.

To ensure the leadless cardiac pacemaker functions correctly, a specific minimum internal supply voltage is maintained. When pacing tank capacitor charging occurs, the supply voltage can drop from a pre-charging level which can become more significant when the battery nears an end-of-life condition and has reduced current sourcing capability. Therefore, a leadless cardiac pacemaker can be constructed with a capability to stop charging the pacing tank capacitor when the supply voltage drops below a specified level. When charging ceases, the supply voltage returns to the value prior to the beginning of tank capacitor charging.

In another technique, the charge current can be lowered to prevent the supply voltage from dropping below the specified level. However, lowering the charge current can create difficulty in ensuring pacing rate or pacing pulse amplitude are maintained, since the lower charge current can extend the time for the pacing tank capacitor to reach a target voltage level.

The illustrative scheme for transmitting data does not significantly increase the current consumption of the pacemaker. For example, the pacemaker could transmit data continuously in a loop, with no consumption penalty.

The illustrative example avoids usage of radiofrequency (RF) communication to send pacing instructions to remote electrodes on a beat-to-beat basis to cause the remote electrodes to emit a pacing pulse. RF communication involves use of an antenna and modulation/demodulation unit in the remote electrode, which increase implant size significantly. Also, communication of pacing instructions on a beat-to-beat basis increases power requirements for the main body and the remote electrode. In contrast, the illustrative system and stimulator do not require beat-to-beat communication with any controlling main body.

The illustrative leadless pacemaker 102 includes an internal power source that can supply all energy for operations and pulse generation. In contrast, some conventional implanted pulse generators have remote pacing electrodes that receive some or all energy from an energy source through an RF induction technique, an energy transfer scheme that employs a large loop antenna on the remote electrode which increases size significantly. In addition, energy transfer with the RF induction technique is inefficient and is associated with a significant increase in battery size of the energy source. In contrast, the illustrative leadless pacemaker 102 uses an internal battery and does not require energy to be drawn from outside sources. Also in the conventional system, the energy source receives sensing information by RF communication from the remote electrodes and sends pacing instructions to the electrodes on a beat-to-beat basis in a configuration that uses an addressing scheme in which the identity of specific remote pacing electrodes is stored in the energy source memory. The conventional method can also be inefficient due to overhead for transmitting an identification number from/to a generic pacing electrode at implant and/or during sensing. The illustrative leadless pacemaker 102 avoids such overhead through a structure in which pulse generation functionality is independent within a single implantable body.

Another conventional technology uses a system of addressable remote electrodes that stimulate body tissue without requiring a main body to send commands for individual stimulations. The remote electrodes are specified to be of a size and shape suitable for injection rather than for endocardial implantation. A controller sets operating parameters and sends the parameters to remote electrodes by addressable communication, enabling the remote electrodes function relatively autonomously while incurring some overhead to controller operations. However, the remote electrodes do not sense or monitor cardiac information and rely on the main body to provide sensing functionality. In contrast, the illustrative leadless pacemaker 102 combines pacing and sensing of intrinsic cardiac activity in a single implantable body.

Referring again to FIG. 1B, the circuit 132 for receiving communication via electrodes 108 receives the triggering information as described and can also optionally receive other communication information, either from the other implanted pulse generator 106 or from a programmer outside the body. This other communication could be coded with a pulse-position scheme as described in FIG. 5 or could otherwise be a pulse-modulated or frequency-modulated carrier signal, preferably from 10 kHz to 100 kHz.

With regard to operating power requirements in the leadless cardiac pacemaker 102, for purposes of analysis, a pacing pulse of 5 volts and 5 milliamps amplitude with duration of 500 microseconds and a period of 500 milliseconds has a power requirement of 25 microwatts.

In an example embodiment of the leadless pacemaker 102, the processor 112 typically includes a timer with a slow clock that times a period of approximately 10 milliseconds and an instruction-execution clock that times a period of approximately 1 microsecond. The processor 112 typically operates the instruction-execution clock only briefly in response to events originating with the timer, communication amplifier 134, or cardiac sensing amplifier 132. At other times, only the slow clock and timer operate so that the power requirement of the processor 112 is no more than 5 microwatts.

For a pacemaker that operates with the aforementioned slow clock, the instantaneous power consumption specification, even for a commercially-available micropower microprocessor, would exceed the battery's power capabilities and would require an additional filter capacitor across the battery to prevent a drop of battery voltage below the voltage necessary to operate the circuit. The filter capacitor would add avoidable cost, volume, and potentially lower reliability.

For example, a microprocessor consuming only 100 microamps would require a filter capacitor of 5 microfarads to maintain a voltage drop of less than 0.1 volt, even if the processor operates for only 5 milliseconds. To avoid the necessity for such a filter capacitor, an illustrative embodiment of a processor can operate from a lower frequency clock to avoid the high instantaneous power consumption, or the processor can be implemented using dedicated hardware state machines to supply a lower instantaneous peak power specification.

In a pacemaker, the cardiac sensing amplifier typically operates with no more than 5 microwatts.

An accelerometer amplifier, or other general purpose signal conditioning amplifier, operates with approximately 10 microwatts.

A communication amplifier at 100 kHz operates with no more than 25 microwatts. The battery ammeter and battery voltmeter operate with no more than 1 microwatt each.

A pulse generator typically includes an independent rate limiter with a power consumption of no more than 2 microwatts.

The total power consumption of the pacemaker is thus 74 microwatts, less than the disclosed 75-microwatt battery output.

Improvement attained by the illustrative cardiac pacing system 100 and leadless cardiac pacemaker 102 is apparent.

The illustrative cardiac pacing system 100 enables encoding optional outgoing communication in the pacing pulse, so that the outgoing communication power requirement does not exceed the pacing current requirement, approximately 25 microwatts.

The illustrative leadless cardiac pacemaker 102 can have sensing and processing circuitry that consumes no more than 10 microwatts as in conventional pacemakers.

The described leadless cardiac pacemaker 102 can have an incoming communication amplifier for receiving triggering signals and optionally other communication which consumes no more than 25 microwatts.

Furthermore, the leadless cardiac pacemaker 102 can have a primary battery that exhibits an energy density of at least 3 watt-hours per cubic centimeter (W·h/cc).

Figure 7:
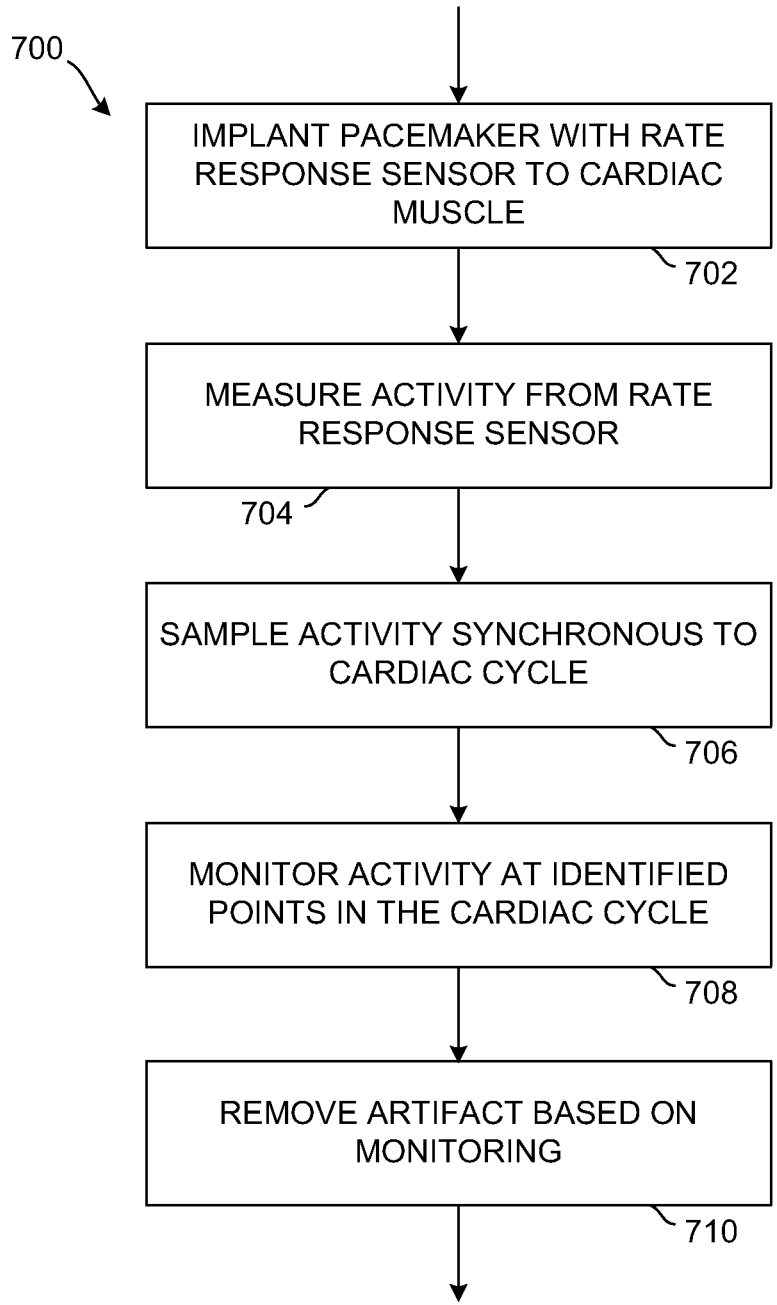
FIG. 7 is a schematic flow chart depicting an embodiment of a method for operating an activity sensor in a rate-responsive cardiac pacemaker.

Referring to FIG. 7, a schematic flow chart depicts an embodiment of a method 700 for operating an activity sensor in a rate-responsive cardiac pacemaker. A leadless cardiac pacemaker that includes a rate-response sensor is implanted 702 in contact with cardiac muscle. An activity signal is measured 704 using the rate-response sensor. The activity signal includes an artifact signal that results from cardiac muscle motion. The activity signal is sampled 706 synchronously with a cardiac cycle. The activity signal is monitored 708 at identified points in the cardiac cycle. The artifact signal is removed 710 from the activity signal based on the monitoring. In various embodiments, the activity signal can be measured using an accelerator, thermistor, or pressure sensor.

Figure 8:
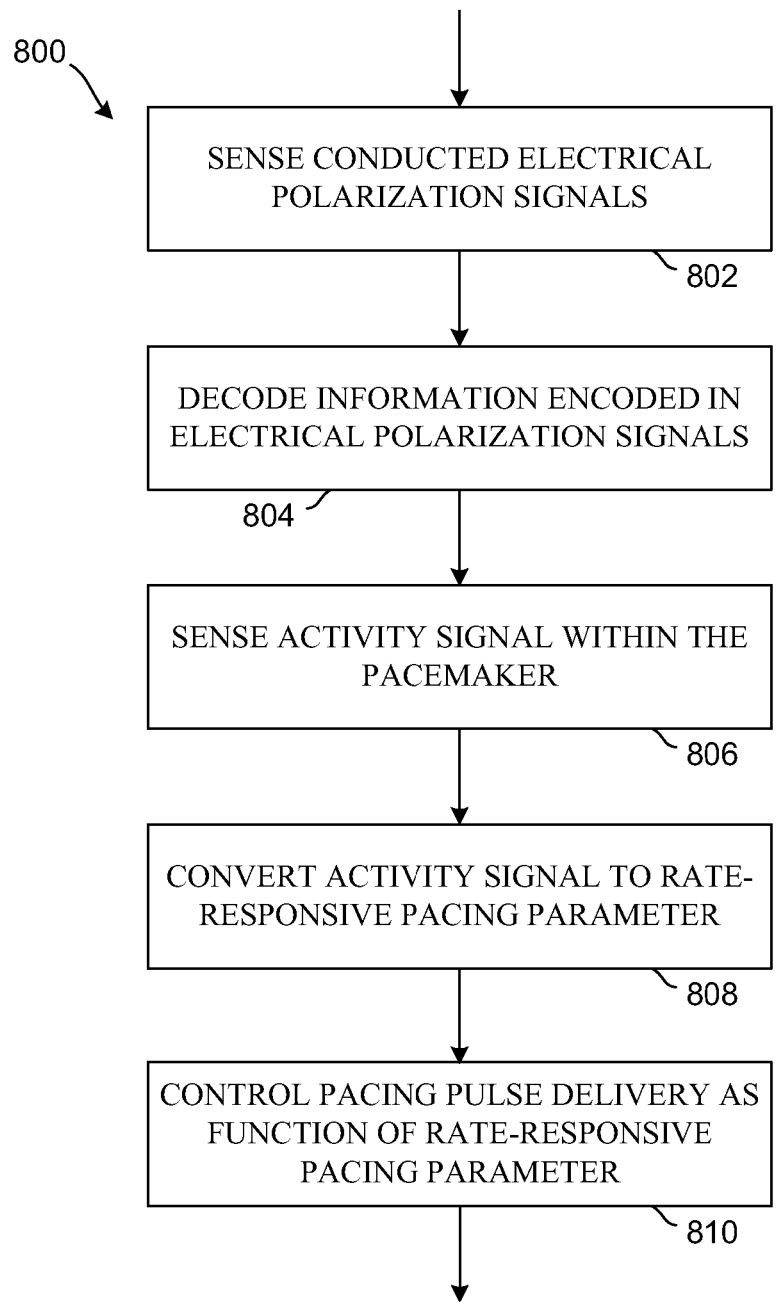
FIG. 8 is a schematic flow chart showing an embodiment of a method for communicating information for setting control parameters for an activity sensor in a cardiac pacing system.

Referring to FIG. 8, a schematic flow chart depicts an embodiment of a method 800 for setting operating parameters in a rate-responsive cardiac pacemaker. The method 800 comprises sensing 802 electrical signals conducted through a patient's body, decoding 804 information encoded in the electrical signals, and storing the result. An activity signal is sensed 806 within the pacemaker. The activity sensor signal is converted 808 to a rate-responsive pacing parameter as a function of the stored information encoded in the electrical signals. Pacing pulse delivery is controlled 810 as a function of the rate-responsive pacing parameter.

In some embodiments, information is encoded, for example, as a binary code in one or more notches interrupting a stimulation pulse. Information can otherwise or also be encoded in selected or designated codes as variations in pacing pulse width of a stimulation pulse. Information can also be conveyed as electrical energy in a stimulation pulse in designated codes encoding the information in modulation of off-time between pacing pulses.

Terms "substantially", "essentially", or "approximately", that may be used herein, relate to an industry-accepted tolerance to the corresponding term. Such an industry-accepted tolerance ranges from less than one percent to twenty percent and corresponds to, but is not limited to, component values, integrated circuit process variations, temperature variations, rise and fall times, and/or thermal noise. The term "coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. Inferred coupling, for example where one element is coupled to another element by inference, includes direct and indirect coupling between two elements in the same manner as "coupled".

While the present disclosure describes various embodiments, these embodiments are to be understood as illustrative and do not limit the claim scope. Many variations, modifications, additions and improvements of the described embodiments are possible. For example, those having ordinary skill in the art will readily implement the steps necessary to provide the structures and methods disclosed herein, and will understand that the process parameters, materials, and dimensions are given by way of example only. The parameters, materials, and dimensions can be varied to achieve the desired structure as well as modifications, which are within the scope of the claims. Variations and modifications of the embodiments disclosed herein may also be made while remaining within the scope of the following claims. For example, although the description has some focus on CRT, the pacemaker, system, structures, and techniques can otherwise be applicable to other uses, for example multi-site pacing for prevention of tachycardias in the atria or ventricles. Phraseology and terminology employed herein are for the purpose of the description and should not be regarded as limiting. With respect to the description, optimum dimensional relationships for the component parts are to include variations in size, materials, shape, form, function and manner of operation, assembly and use that are deemed readily apparent and obvious to one of ordinary skill in the art and all equivalent relationships to those illustrated in the drawings and described in the specification are intended to be encompassed by the present description. Therefore, the foregoing is considered as illustrative only of the principles of structure and operation. Numerous modifications and changes will readily occur to those of ordinary skill in the art whereby the scope is not limited to the exact construction and operation shown and described, and accordingly, all suitable modifications and equivalents may be included.

What is claimed is:

1. A method of pacing a patient's heart, comprising:
    sensing a parameter with a sensor hermetically contained within a housing of a leadless pacemaker implanted in the heart, wherein the leadless pacemaker comprises a plurality of electrodes formed integrally to the housing or coupled to the housing at a maximum distance of 2 centimeters;
    generating electrical pulses with a pulse delivery system hermetically contained within the housing of the leadless pacemaker;
    delivering the electrical pulses through the electrodes of the leadless pacemaker to stimulate the heart at least partly based on the sensed parameter;
    generating encoded information signals within the leadless pacemaker;
    directly communicating the encoded information signals from the leadless pacemaker during a cardiac refractory period of the heart to a device external to the patient through the electrodes of the leadless pacemaker; and
    sourcing energy of no more than 75-80 microwatts instantaneously for generating the electrical pulses using a battery, wherein the peak power of the leadless pacemaker is less than or equal to 74 microwatts.

2. The method of claim 1 wherein the delivering step further comprises delivering the electrical pulses to the heart through electrodes of the leadless pacemaker at least partly based on the sensed parameter and partly based on communication signals received via the electrodes.

3. The method of claim 1 wherein the sensing step further comprises sensing temperature with the sensor of the leadless pacemaker.

4. The method of claim 1 wherein the sensing step further comprises sensing pressure with the sensor of the leadless pacemaker.

5. The method of claim 1 wherein the information signals are selected from a group consisting of programmable parameter settings, event counts, power-supply voltage, power-supply current, and rate-response control parameters adapted for converting a sensor signal to a rate-responsive pacing parameter.

6. The method of claim 1 wherein the communicating step further comprises communicating encoded information signals to the device in designated codes encoding the information in pacing pulse width.

7. The method of claim 1 further comprising:
    invoking a low-gain setting in a receiving amplifier/filter of the leadless pacemaker for normal operation and detecting presence of at least one pulse; and
    invoking a high-gain setting for detecting and decoding information encoded in the detected at least one pulse.

8. The method of claim 1, wherein the step of generating encoded information signals within the leadless pacemaker comprises generating notches in at least one timing window of at least one pacing pulse as the encoded information.

9. A method of pacing a patient's heart, comprising:
    sensing a parameter with a sensor hermetically contained within a housing of a leadless pacemaker implanted in the heart, wherein the leadless pacemaker comprises a plurality of electrodes formed integrally to the housing or coupled to the housing at a maximum distance of 2 centimeters;
    generating electrical pulses with a pulse delivery system hermetically contained within the housing of the leadless pacemaker;
    delivering the electrical pulses through the electrodes of the leadless pacemaker to stimulate the heart at least partly based on the sensed parameter;
    generating encoded information signals within the leadless pacemaker;
    directly communicating the encoded information signals from the leadless pacemaker during a cardiac refractory period of the heart to a device external to the patient through the electrodes of the leadless pacemaker, wherein the sensor is configured to operate with a power requirement of no more than 10 microwatts.

* * * * *